(12) United States Patent
Uchida et al.

(10) Patent No.: US 11,633,086 B2
(45) Date of Patent: Apr. 25, 2023

(54) EXTERNAL MECHANISM FOR ENDOSCOPE, AND ENDOSCOPE APPARATUS

(71) Applicant: OLYMPUS CORPORATION, Tokyo (JP)

(72) Inventors: Ramiya Uchida, Tachikawa (JP); Masanobu Koitabashi, Hachioji (JP); Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 22 days.

(21) Appl. No.: 17/094,191

(22) Filed: Nov. 10, 2020

(65) Prior Publication Data

US 2021/0105385 A1    Apr. 8, 2021

Related U.S. Application Data

(63) Continuation of application No. PCT/JP2019/007912, filed on Feb. 28, 2019.

(30) Foreign Application Priority Data

May 24, 2018  (JP) .............................. JP2018-099602

(51) Int. Cl.
*A61B 1/00* (2006.01)
*H04N 5/225* (2006.01)
*A61B 1/005* (2006.01)

(52) U.S. Cl.
CPC ...... *A61B 1/00105* (2013.01); *A61B 1/00042* (2022.02); *H04N 5/2253* (2013.01);
(Continued)

(58) Field of Classification Search
CPC .......... H04N 5/2253; H04N 2005/2255; A61B 1/00133; A61B 1/0014; A61B 1/0052;
(Continued)

(56) References Cited

U.S. PATENT DOCUMENTS 5,989,182 A * 11/1999 Hori ..................... A61B 1/0052
                                                600/173
6,047,431 A *  4/2000 Canonica ................ B08B 9/045
                                                15/104.095
(Continued)

FOREIGN PATENT DOCUMENTS

EP       1 623 662 A1    2/2006
EP       1 955 646 A1    8/2008
(Continued)

OTHER PUBLICATIONS

International Search Report dated May 21, 2019 received in PCT/JP2019/007912.

*Primary Examiner* — Howard D Brown, Jr.
(74) *Attorney, Agent, or Firm* — Scully, Scott, Murphy & Presser, P.C.

(57) ABSTRACT

An external mechanism for an endoscope includes: a bending wheel configured to engage with a second UD knob of a second bending operation device provided in an operation portion of an endoscope; a motor portion configured to generate a driving force for rotating the bending wheel; a housing case housing the bending wheel and the motor portion and detachably attached to the operation portion, and an operation switch arranged outside the housing case and configured to output a control signal to the motor portion due to the operating element being operated, in which the operation switch is pivotally supported by the rotation shaft and rotates with respect to the housing case.

12 Claims, 13 Drawing Sheets

(52) U.S. Cl.
CPC .......... *A61B 1/0014* (2013.01); *A61B 1/0052* (2013.01); *A61B 1/00133* (2013.01); *H04N 2005/2255* (2013.01)

(58) Field of Classification Search
CPC .............. A61B 1/00039; A61B 1/0016; A61B 1/00105; G02B 23/24
See application file for complete search history.

(56) References Cited

U.S. PATENT DOCUMENTS

| | | | | |
|---|---|---|---|---|
| 9,044,163 | B2* | 6/2015 | Yamaguchi | A61B 5/1459 |
| 2001/0037051 | A1* | 11/2001 | Fujii | A61B 1/0052 |
| | | | | 600/146 |
| 2004/0073084 | A1* | 4/2004 | Maeda | A61B 1/00042 |
| | | | | 600/101 |
| 2005/0125009 | A1* | 6/2005 | Perry | A61B 17/2909 |
| | | | | 606/139 |
| 2006/0100485 | A1* | 5/2006 | Arai | A61B 1/00068 |
| | | | | 600/101 |
| 2006/0173240 | A1* | 8/2006 | Fukuyama | A61B 1/043 |
| | | | | 600/118 |
| 2009/0062616 | A1* | 3/2009 | Nagamizu | A61B 1/00096 |
| | | | | 600/173 |
| 2013/0006053 | A1* | 1/2013 | Yamakawa | A61B 1/0016 |
| | | | | 600/114 |
| 2018/0035878 | A1* | 2/2018 | Nara | A61B 1/0011 |
| 2019/0380562 | A1* | 12/2019 | Deuel | A61B 1/00131 |
| 2020/0146534 | A1* | 5/2020 | Harada | A61B 1/00042 |
| 2020/0297189 | A1* | 9/2020 | Ikeda | A61B 1/0057 |

FOREIGN PATENT DOCUMENTS

| | | |
|---|---|---|
| EP | 3 202 302 A1 | 8/2017 |
| EP | 3 272 272 A1 | 1/2018 |
| JP | 05-300873 A | 11/1993 |
| JP | 2002-136467 A | 5/2002 |
| JP | 2002-248073 A | 9/2002 |
| JP | 2003-305000 A | 10/2003 |
| JP | 2004-337188 A | 12/2004 |
| JP | 2008-048788 A | 3/2008 |
| JP | 6053999 B2 | 12/2016 |
| WO | 2004/098394 A1 | 11/2004 |
| WO | 2017/134884 A1 | 8/2017 |

* cited by examiner

EXTERNAL MECHANISM FOR ENDOSCOPE, AND ENDOSCOPE APPARATUS

CROSS REFERENCE TO RELATED APPLICATION

This application is a continuation application of PCT/JP2019/007912 filed on Feb. 28, 2019 and claims benefit of Japanese Application No. 2018-099602 filed in Japan on May 24, 2018, the entire contents of which are incorporated herein by this reference.

BACKGROUND OF THE INVENTION

1. Field of the Invention

The present invention relates to an external mechanism for an endoscope and an endoscope apparatus, in which an external unit including an operation switch is attached to a bending operation knob of an endoscope to thereby rotate the bending operation knob by a driving force and bend a bending portion provided in an insertion portion.

2. Description of the Related Art

Endoscopes have been used in the medical field, industrial field, and the like. The endoscope includes a bending portion in an elongated insertion portion that is inserted into a subject.

Japanese Unexamined Patent Application Publication No. 5-300873 discloses an endoscope bending control device capable of using a manual angle type endoscope as an electric angle control type endoscope, the manual angle type endoscope being capable of orienting an endoscope distal end portion in a desired direction when a UD angle knob and an RL angle knob located on one side of an operation portion is rotated by a manual operation and then an endoscope bending portion bends in an arbitrary direction.

The above-described bending control device for an endoscope includes a UD angle knob driving motor and an RL angle knob driving motor in a main body portion, and a UD angle switch and an RL angle switch are provided on a side portion of the main body portion. The main body portion is detachable from the operation portion, and engagement portions provided in the respective angle knob driving motors are engaged with the respective angle knobs in a state in which the main body portion is fixed to the operation portion.

The respective angle switches are operated by a user to rotate the respective angle knob driving motors forward or reverse, and stop, whereby the endoscope distal end portion can be oriented in a desired direction by operating the respective angle knobs.

Japanese Unexamined Patent Application Publication No. 2008-48788 discloses an endoscope that includes a first bending portion and a second bending portion arranged in parallel along an extending direction of an insertion portion on a distal end side of the elongated insertion portion, and is provided with a main bending operation device and a sub-bending operation device on an operation portion located on a proximal end side of the insertion portion. In such an endoscope, a bending operation of the first bending portion is performed by rotation-operating an operation knob of the main bending operation device, and a bending operation of the second bending portion is performed by rotation-operating an operation knob of the sub-bending operation device.

Therefore, it is possible for the user to smoothly insert the insertion portion into a tubular body cavity that is bent in a complicated manner by performing the rotation-operation independently for each operation knob to bend the first bending portion or the second bending portion, and it is possible to easily orient an observation optical system built in the distal end side of the insertion portion in a desired direction.

In the operation portion described above, the sub-bending operation device is provided so as to be spaced apart from the main bending operation device on the proximal end side of the operation portion on the side opposite to the insertion portion from the main bending operation device.

Further, an external electric bending mechanism that is attachable to and detachable from the operation portion, and is configured to rotate, for example, the sub-bending operation device by a driving force of a drive source such as a motor in an attached state has been devised.

In the above-described external electric bending mechanism, an operation switch for operating the drive source in the attached state is required. It is conceivable to provide an angle switch as shown in Japanese Unexamined Patent Application Publication No. 5-300873 as an operation switch on the side of the main body portion of the external electric bending mechanism.

Japanese Patent No. 6053999 discloses a bending operation mechanism having a compact and lightweight watertight structure and an endoscope including the bending operation mechanism.

Therefore, it is conceivable to cover the above-described angle switch and its surroundings with a cover member and to prevent contamination of the angle switch during use of the endoscope.

SUMMARY OF THE INVENTION

An external mechanism for an endoscope according to an aspect of the present invention includes an engagement member configured to engage with an operation knob of a bending operation device provided in an operation portion of an endoscope, a drive source configured to generate a driving force for rotating the engagement member, a housing case housing the engagement member and the drive source and detachably attached to the operation portion, and an operation switch arranged outside the housing case and configured to output a control signal to the drive source due to an operating element being operated, in which the operation switch is pivotally supported by a rotation shaft and rotates with respect to the housing case.

In the endoscope apparatus according to one aspect of the present invention, the external mechanism for an endoscope according to the aspect is mounted.

An external mechanism for an endoscope according to another aspect of the present invention includes an engagement member configured to engage with an operation knob of a bending operation device provided in an operation portion of the endoscope, a drive source configured to generate a driving force for rotating the engagement member, a housing case housing the engagement member and the drive source and detachably attached to the operation portion, and an operation switch arranged outside the housing case and configured to output a control signal to the drive source due to an operating element being operated, in which the operation switch includes a dummy switch, and the dummy switch enables, due to being disposed on an actuating switch actuating a predetermined function of the endoscope provided in an operation portion of the endoscope, the actuating switch to be activated.

In the endoscope apparatus according to another aspect of the present invention, the external mechanism for an endoscope according to the other aspect is mounted.

DETAILED DESCRIPTION OF THE PREFERRED EMBODIMENT

Figure 1:
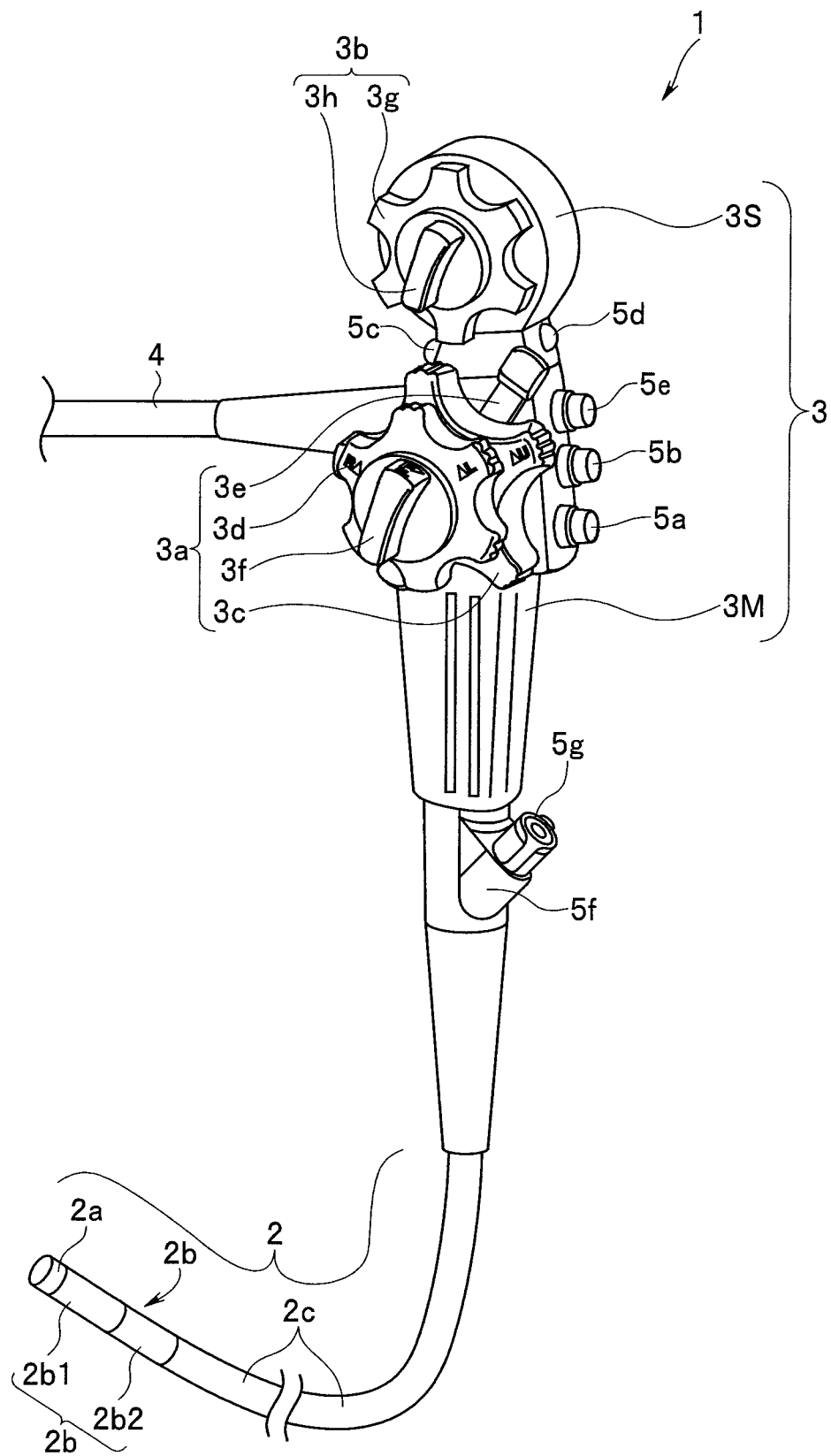
FIG. 1 is a diagram illustrating an endoscope including a sub-operation portion.

Hereinafter, an embodiment of the present invention will be described with reference to the accompanying drawings.

Note that, in each drawing used in the following description, in order to make each of the components large enough to be recognizable in the drawings, there are some cases where the components are different from each other in terms of scale. In other words, the present invention is not limited to the number of components described in these drawings, the shape of the components, the ratio of the sizes of the components, and the relative positional relationship between each of the components.

A configuration of an endoscope will be described with reference to FIG. 1.

An endoscope 1 illustrated in FIG. 1 includes an elongated insertion portion 2, an operation portion 3 also serving as a grasping portion, and a universal cord 4. In the insertion portion 2, a distal end portion 2a, a bending portion 2b, and a flexible tube portion 2c having an elongated shape with flexibility are continuously provided in this order from the distal end side.

In the present embodiment, the bending portion 2b has a first bending portion 2b1 and a second bending portion 2b2. The first bending portion 2b1 is provided on a distal end side of the insertion portion 2. The second bending portion 2b2 is continuously provided to a proximal end portion of the first bending portion 2b1 via a connection portion (not illustrated). The first bending portion 2b1 is bendable in, for example, an up-down direction and a right-left direction. Meanwhile, the second bending portion 2b2 is bendable in the up-down direction.

The operation portion 3 includes a first bending operation device 3a and a second bending operation device 3b. In the present embodiment, the operation portion 3 has a main operation portion 3M which also serves as a grasping portion and in which the first bending operation device 3a is provided, and a sub-operation portion 3S which is provided on a proximal end side of the main operation portion 3M and in which the second bending operation device 3b is provided. The second bending operation device 3b is provided so as to be spaced apart from the first bending operation device 3a on an operation portion proximal end side which is a side opposite to the insertion portion 2.

The first bending operation device 3a has a first bending portion up-down operation knob (hereinafter, shortly referred to as a first UD knob) 3c and a first bending portion right-left operation knob (hereinafter, shortly referred to as a first RL knob) 3d, and a first bending portion up-down direction fixing lever (hereinafter, shortly referred to as a first UD fixing lever) 3e and a first bending portion right-left direction fixing knob (hereinafter, shortly referred to as a first RL fixing knob) 3f, respectively, as bending operation knobs.

The second bending operation device 3b has a second bending portion up-down operation knob (hereinafter shortly referred to as a second UD knob) 3g that is the bending operation knob, and a second bending portion up-down direction fixing knob (hereinafter, shortly referred to as a second UD fixing knob) 3h.

The first UD knob 3c is rotated when the first bending portion 2b1 is bending-operated in the up-down direction. The first RL knob 3d is rotated when the first bending portion 2b1 is bending-operated in the right-left direction. The first UD fixing lever 3e can be switched between a free position and a fixed position. The first RL fixing knob 3f can be switched between a free position and a fixed position.

When the first UD fixing lever 3e is in the free position, the first UD knob 3c is rotatably operated. At the time, the first bending portion 2b1 is in a state in which the first bending portion 2b1 is bent in an upward direction or a downward direction in accordance with the rotating operation of the first UD knob 3c. Meanwhile, when the first RL fixing knob 3f is in the free position, the first RL knob 3d is rotatably operated. At the time, the first bending portion 2b1 is in a state in which the first bending portion 2b1 is bent in a leftward direction or a rightward direction in accordance with the rotating operation of the first RL knob 3d.

On the other hand, when the first UD fixing lever 3e is switched to the fixed position, the rotation of the first UD knob 3c is restricted. As a result, the bending state of the first bending portion 2b1 in the up-down direction is held in the state at the time of switching. Similarly, when the first RL fixing knob 3f is switched to the fixed position, the rotation of the first RL knob 3d is restricted. As a result, the bending state of the first bending portion 2b1 in the right-left direction is held in the state at the time of switching.

A second UD knob 3g is rotated when the second bending portion 2b2 is bending-operated in the up-down direction. The second UD fixing knob 3h can be switched between a free position and a fixed position.

When the second UD fixing knob 3h is in the free position, the second UD knob 3g is rotatably operated. At the time, the second bending portion 2b2 is in a state in which the second bending portion 2b2 is bent in the upward direction or the downward direction in accordance with the rotating operation of the second UD knob 3g. On the other hand, when the second UD fixing knob 3h is switched to the fixed position, the rotation of the second UD knob 3g is restricted. As a result, the bending state of the second bending portion 2b2 in the up-down direction is held in the state at the time of switching.

Note that reference numeral 5a denotes an air/water feeding button, reference numeral 5b denotes a suction operation button, reference numerals 5c, 5d, and 5e each denote a remote switch, reference numeral 5f denotes a treatment tool insertion port, and reference numeral 5g denotes a forceps plug. The remote switch is a switch for stopping an endoscope image displayed on a screen of a display device (not illustrated), or for performing recording, image enlargement, switching of illumination light, and the like, and an optimal function is allocated to each switch.

Figure 2A:
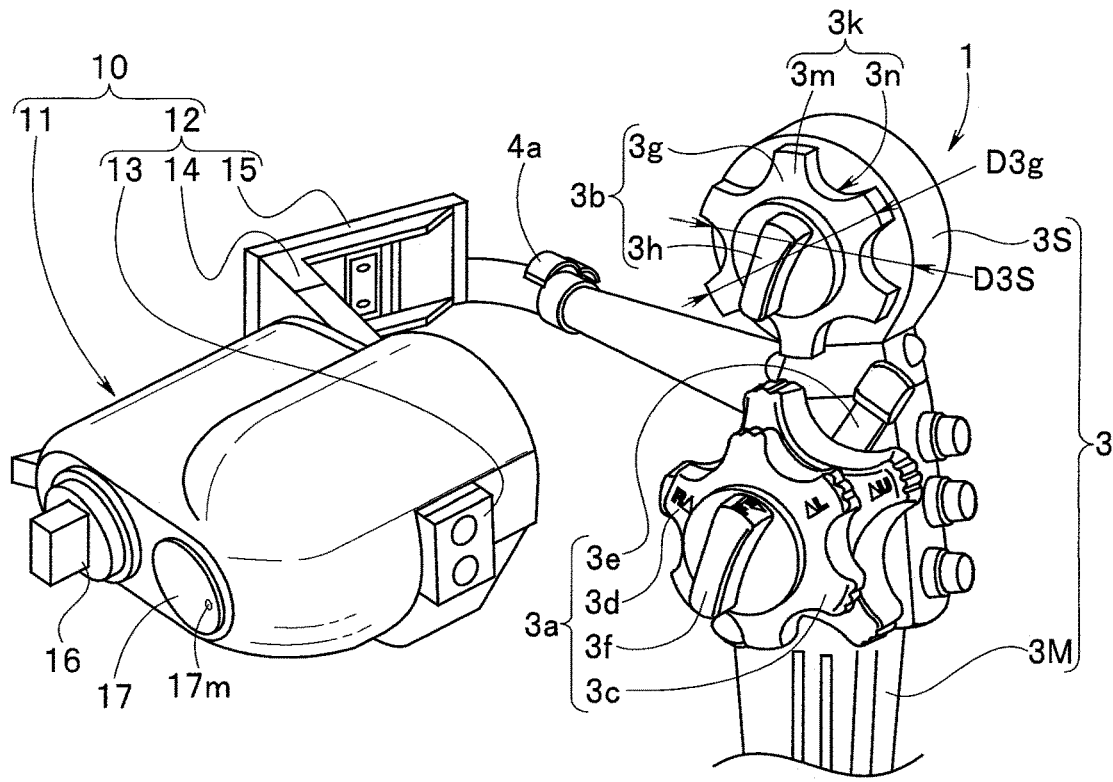
FIG. 2A is a diagram illustrating a relationship between the sub-operation portion included in the endoscope and an endoscope external mechanism.

In FIG. 2A, reference numeral 10 denotes an endoscope external mechanism. The endoscope external mechanism 10 is attached to the sub-operation portion 3S of the endoscope 1, whereby an endoscope apparatus of the present invention is configured. The endoscope external mechanism 10 is detachably attached to the second UD knob 3g provided in the sub-operation portion 3S. The endoscope external mechanism 10 is an auxiliary mechanism portion that is attached to the second UD knob 3g and rotates the second UD knob 3g by a driving force of a motor (see reference numeral 32 in FIG. 4B) to be described later.

Reference numeral 11 denotes a housing case, and reference numeral 12 denotes a case attachment/detachment fixing portion (hereinafter referred to as a case attaching/detaching portion). The case attaching/detaching portion 12 includes a locking portion 13, a hinge portion 14, and a locking claw portion 15.

The locking portion 13 is fixedly provided at a predetermined position of the housing case 11. The hinge portion 14 has a substantially L-shape, and one end portion thereof is rotatably disposed at a predetermined position in the housing case 11. The locking claw portion 15 is provided at the other end portion of the L-shaped hinge portion 14.

The rotating state of the hinge portion 14 is restricted by engaging and fixing the locking claw portion 15 to the locking portion 13. Reference numeral 16 denotes a switching knob, and reference numeral 17 denotes a bending state display portion. The bending state display portion 17 includes a rotation index 17m.

Figure 2B:
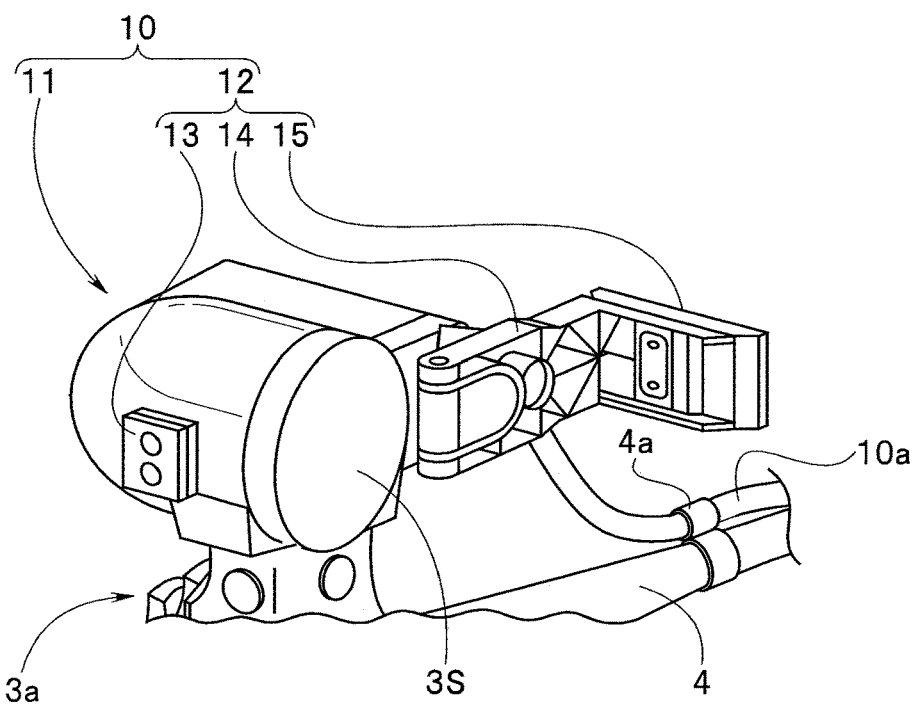
FIG. 2B is a diagram illustrating a state in which the endoscope external mechanism is arranged in the sub-operation portion.

Reference numeral 4a denotes a cable attachment, and one or more cable attachments are provided at a desired position of the universal cord 4 as illustrated in FIG. 2B. A signal cable 10a extended out from the endoscope external mechanism 10 is attached to the cable attachment 4a.

Figure 2C:
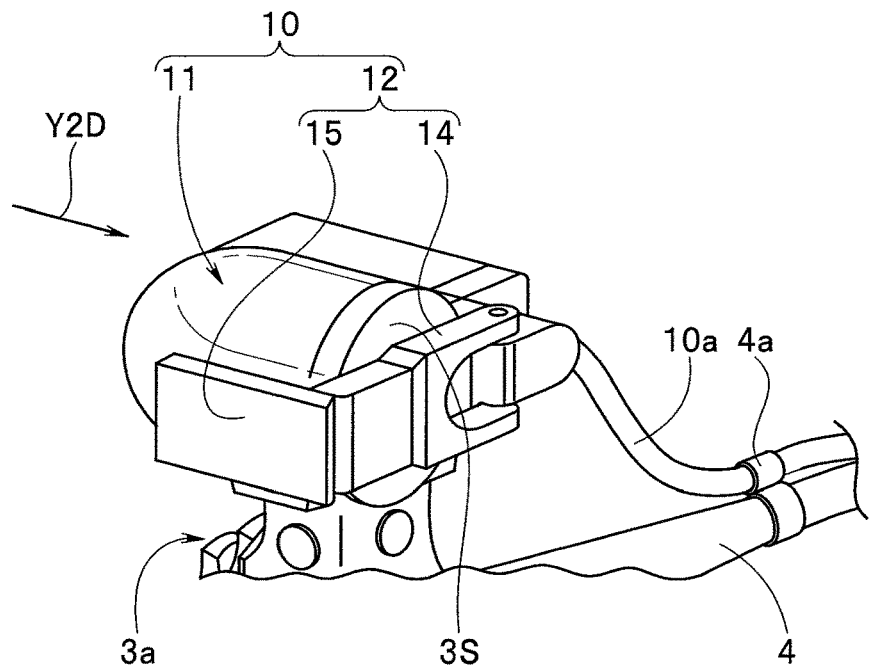
FIG. 2C is a diagram illustrating a state in which the endoscope external mechanism is attached to the sub-operation portion.
Figure 2D:
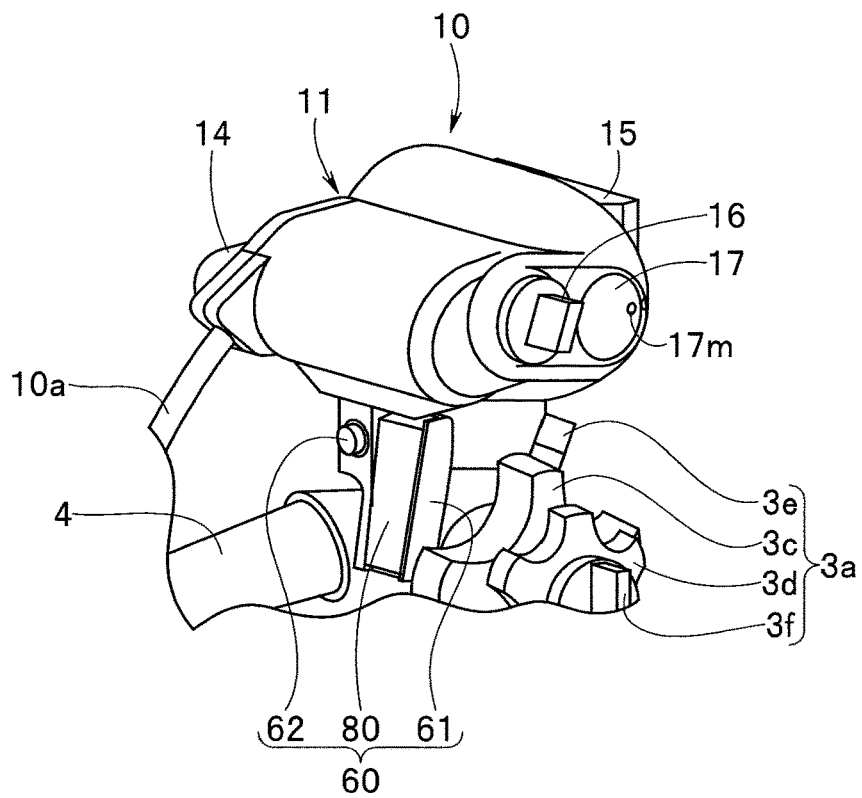
FIG. 2D is a diagram illustrating the sub-operation portion in FIG. 2C as viewed from a direction of an arrow Y2D.

As illustrated in FIG. 2B, in a state in which the housing case 11 covers the second UD knob 3g and is disposed in the sub-operation portion 3S, the endoscope external mechanism 10 is integrally attached to the sub-operation portion 3S by rotating the hinge portion 14 on the one end portion side thereof as a fulcrum and engaging and fixing the locking claw portion 15 with the locking portion 13, as illustrated in FIG. 2C and FIG. 2D.

Note that in FIG. 2D, reference numeral 60 denotes an operation switch. The operation switch 60 is arranged outside the housing case 11. The operation switch 60 has a switch main body 61 and a cover 80 that covers an operating element (reference numeral 70 in FIG. 6) that is not illustrated. Reference numeral 62 denotes a dummy switch.

A configuration of the endoscope external mechanism 10 will be described.

Figure 3:
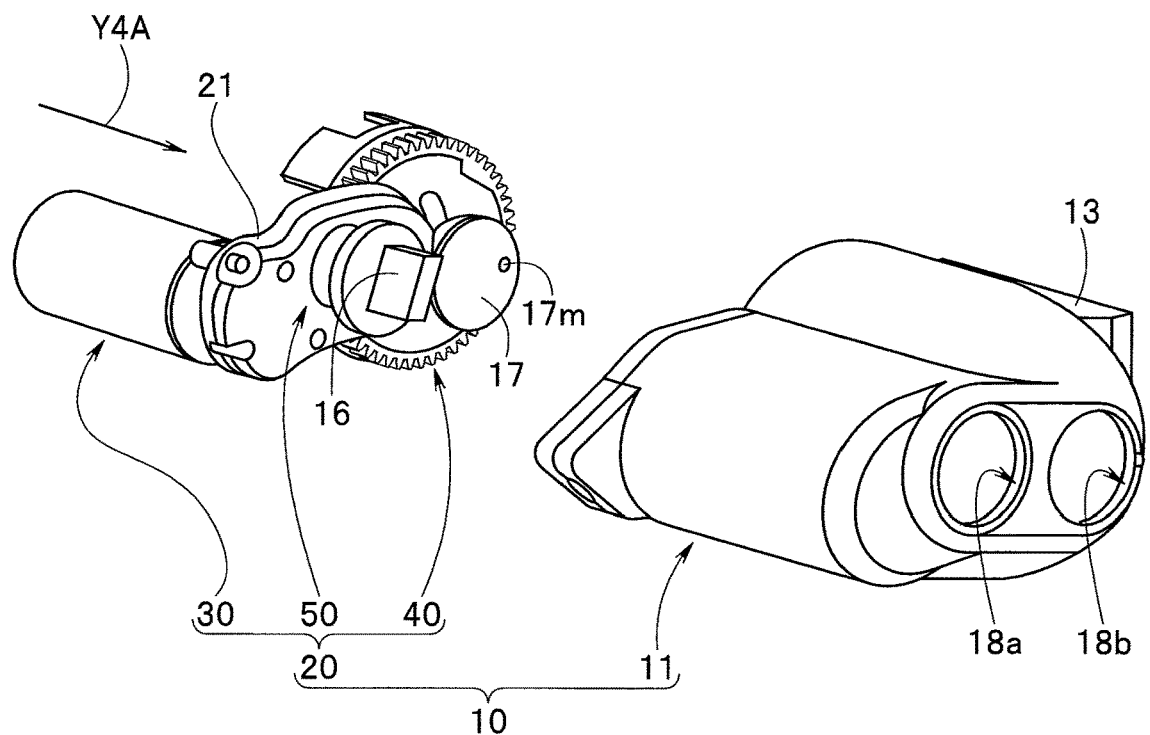
FIG. 3 is a diagram illustrating a relationship between a housing case of the endoscope external mechanism and a knob rotation mechanism housed in the housing case.

As illustrated in FIG. 3, the endoscope external mechanism 10 is configured to house a knob rotation mechanism 20 in a case inner space of the housing case 11. The housing case 11 is provided with a first through-hole 18a and a second through-hole 18b. A switching knob 16 is disposed in the first through-hole 18a, and the bending state display portion 17 is disposed in the second through-hole 18b. The through-holes 18a and 18b communicate with the case inner space and the outside.

The knob rotation mechanism 20 will be described with reference to FIG. 3, FIG. 4A, and FIG. 4B.

As illustrated in FIG. 3, the knob rotation mechanism 20 mainly includes a motor portion 30, a knob rotating portion 40, and a transmission portion 50. Reference numeral 21 illustrated in FIG. 3 to FIG. 4B denotes a rotation mechanism portion main body, and is an attachment member.

Figure 4A:
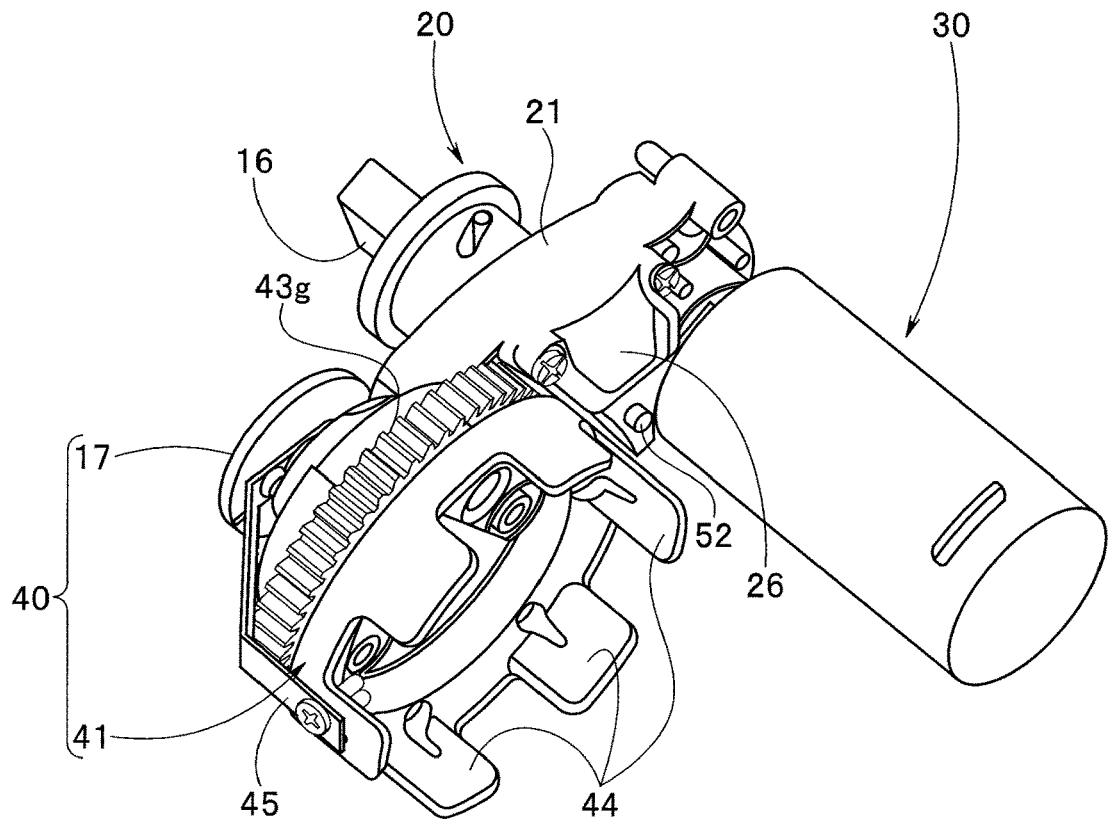
FIG. 4A is a diagram illustrating the knob rotation mechanism as viewed from a direction of an arrow Y4A in FIG. 3.
Figure 4B:
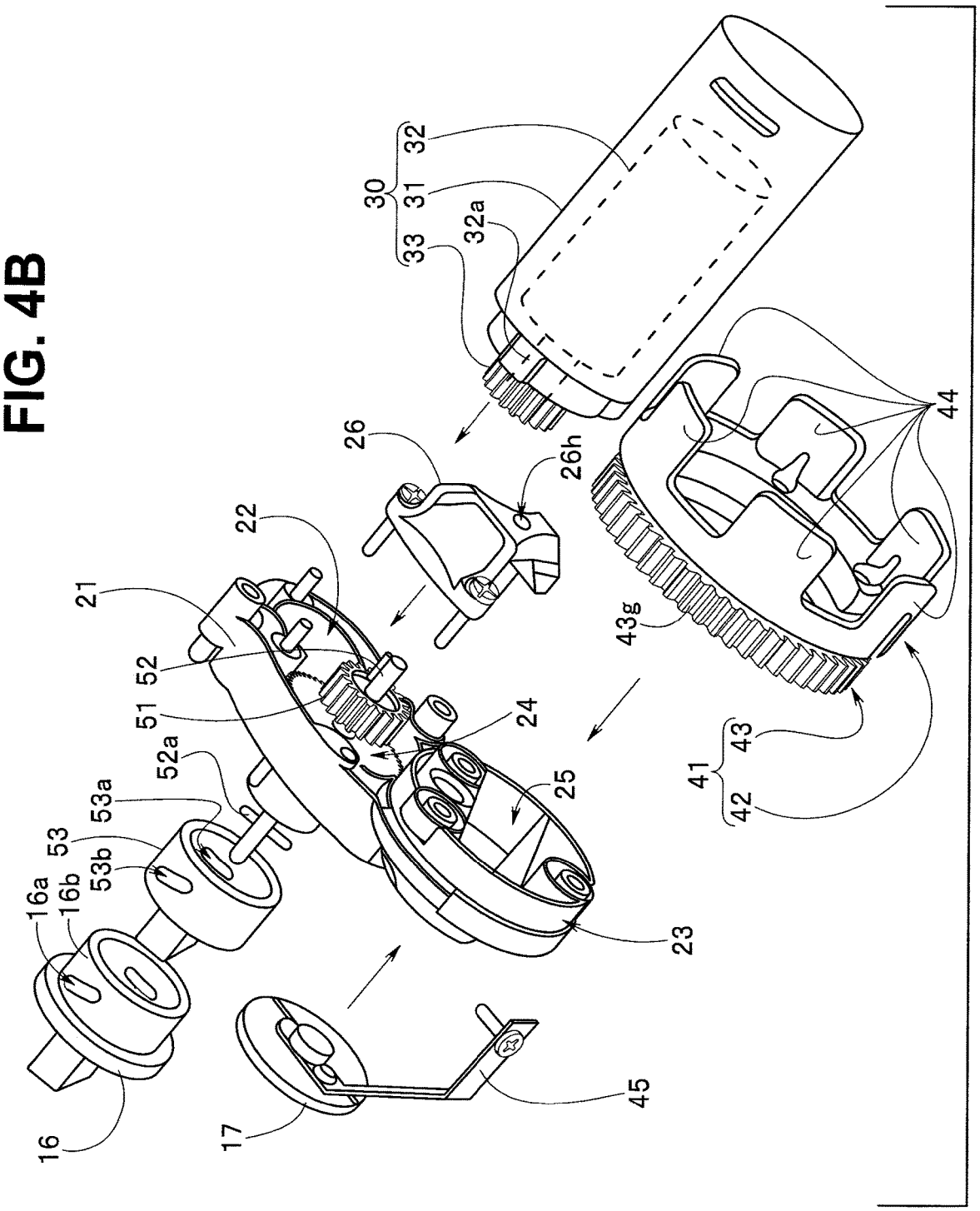
FIG. 4B is an exploded perspective view illustrating an outline of a configuration of the knob rotation mechanism.

As illustrated in FIG. 4B, a motor attachment portion 22, a wheel attachment portion 23, a switching gear attachment portion 24, and the like are respectively provided in a predetermined position in the rotation mechanism portion main body 21.

Reference numeral 25 denotes a recess for a lever. The lever recess 25 is a hole in which an outer shape and a depth are formed so as to house the second UD fixing knob 3*h*. Reference numeral 26 denotes a switching gear support member. The switching gear support member 26 has a through-hole 26*h* in which one end portion of the switching gear shaft 52, at which the switching gear 51 is fixedly provided, is disposed.

The switching gear support member 26 is fixedly provided at a predetermined position of the rotation mechanism portion main body 21. The fixedly provided switching gear support member 26 pivotally supports, in a rotatable manner, the one end portion of the switching gear shaft 52 disposed in the through-hole 26*h*.

The motor portion 30 mainly has a motor case 31, a motor 32 as a drive source indicated by a broken line, and a drive gear 33. The motor 32 is disposed in the motor case 31. The drive gear 33 is fixedly provided at a motor shaft 32*a* that protrudes from the motor 32.

As illustrated in FIG. 4A, the motor case 31 is fixedly provided at the motor attachment portion 22 in a predetermined state.

As illustrated in FIG. 4A and FIG. 4B, the knob rotating portion 40 includes a bending wheel 41 and the bending state display portion 17. The bending wheel 41 has a knob connecting portion 42 and a meshing portion 43. The knob connecting portion 42 is a ring-shaped member. The knob connecting portion 42 and the meshing portion 43 are integrally fixed to each other.

The meshing portion 43 is a gear portion having a gear 43*g* on an outer peripheral surface thereof. A plurality of convex portions 44 are arranged in a circumferential direction on the knob connecting portion 42. The plurality of convex portions 44 are respectively housed in concave portions 3*n* located between convex portions 3*m* of concave and convex portions (reference numeral 3*k* in FIG. 2A) included in the second UD knob 3*g*.

The convex portions 44 are respectively disposed in the concave portions 3*n*, so that the second UD knobs 3*g* and the bending wheels 41 are integrated with each other. In the integrated state, the second UD knob 3*g* is rotated in a rotation direction thereof in accordance with the rotation of the bending wheel 41. The bending wheel 41 is an engagement member that engages with and integrates with the second UD knob 3*g*.

As illustrated in FIG. 3, FIG. 4A, and FIG. 4B, the bending state display portion 17 is a circular plate. As illustrated in FIG. 3, a rotation index 17*m* is provided at a predetermined position on a disk surface of the bending state display portion 17.

In FIG. 4A and FIG. 4B, reference numeral 45 denotes a connecting member. As illustrated in FIG. 4B, one end portion of the connecting member 45 is fixedly provided on a disk back surface of the bending state display portion 17 in an integrated manner. As illustrated in FIG. 4A, the other end portion of the connecting member 45 is fixedly provided at a predetermined position on an outer peripheral surface of the knob connecting portion 42 included in the bending wheel 41 in an integrated manner.

Therefore, the bending state display portion 17 is rotated in the same direction as the bending wheel 41 rotates clockwise or counterclockwise. Therefore, the user can easily determine a bending angle (bending amount) of the second bending portion 2*b*2 by checking the position of the rotation index 17*m*.

Figure 4C:
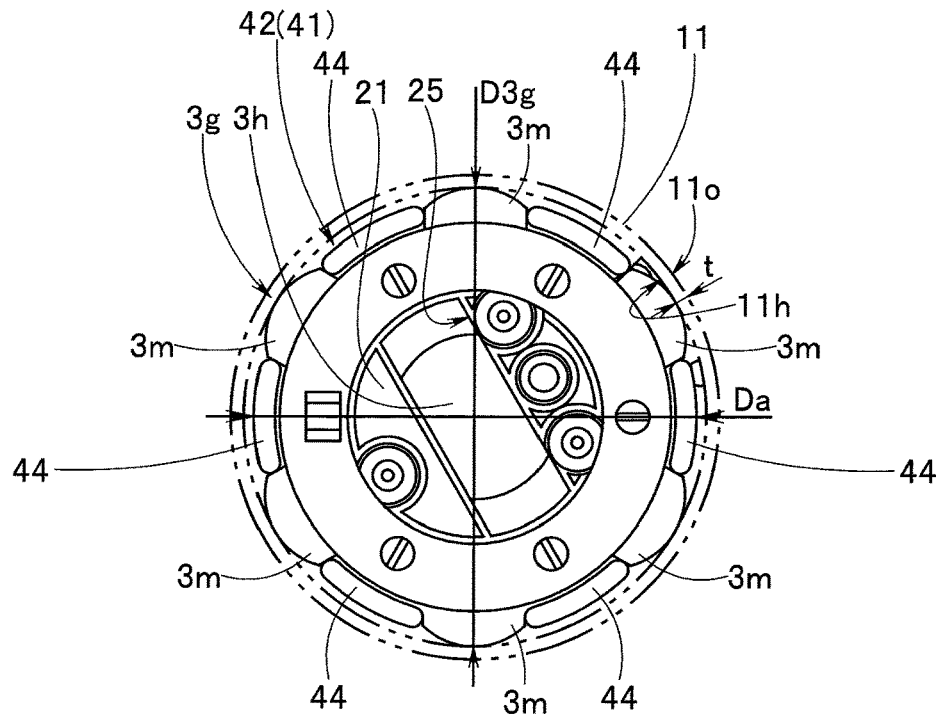
FIG. 4C is a diagram illustrating an attachment state in which a convex portion of a knob connecting portion is disposed in a recess of a second bending portion up-down operation knob in a predetermined state.

An outer diameter Da of the knob connecting portion 42 of the bending wheel 41 is set to be smaller than an outer diameter D3*g* of the second UD knob 3*g*, as illustrated in FIG. 4C in the present embodiment. The knob outer diameter D3*g* of the second UD knob 3*g* is set to be smaller than a circumference outer diameter D3S in advance so that the second UD knob 3*g* is arranged inside an outer peripheral surface (referred to as a circumference outer diameter D3S) of the sub-operation portion 3S as illustrated in FIG. 2A.

Therefore, in a state in which the bending wheel 41 is integrated with the second UD knob 3*g*, an outer peripheral surface of the bending wheel 41 is located closer to the center side than an outer peripheral surface of the second UD knob 3*g*.

Reference numeral 11*h* denotes an inner peripheral surface of a knob rotating portion housing hole portion of the housing case 11. An inner diameter of the inner peripheral surface 11*h* is set to be larger than the outer diameter D3*g* of the second UD knob 3*g* in advance. In addition, a thickness t of the housing case 11 is set in a manner such that an outer peripheral surface 11*o* of the knob rotating portion housing hole portion 11*h* is surface-matched with the outer peripheral surface of the sub-operation portion 3S in the arrangement state.

Note that the outer peripheral surface 11*o* of the knob rotating portion housing hole portion 11*h* may be set to be slightly larger than the outer peripheral surface of the sub-operation portion 3S.

As described above, the outer peripheral surface of the bending wheel 41 is set so as to be arranged closer to the center side than the outer peripheral surface of the second UD knob 3*g*. Further, the thickness of the knob rotating portion housing hole portion 11*h* of the housing case 11 is appropriately set, so that the diameter of the outer peripheral surface 11*o* of the knob rotating portion housing hole portion 11*h* is set to be equal to or slightly larger than the diameter of the outer peripheral surface of the sub-operation portion 3S.

As a result, in a state in which the housing case 11 is reduced in the outer shape to cover the second UD knob 3*g* and is disposed in the sub-operation portion 3S, an adverse effect on an operation of the first UD knob 3*c*, an operation of the first RL knob 3*d*, an operation of the first UD fixing lever 3*e*, and the like can be suppressed due to the outer peripheral surface 11*o* of the knob rotating portion housing hole portion 11*h* of the housing case 11 largely protruding from the outer peripheral surface of the sub-operation portion 3S.

The transmission portion 50 mainly includes a switching gear 51, a switching gear shaft 52, a cam ring 53, and the switching knob 16 illustrated in FIG. 4B. As described above, the switching gear 51 is fixedly provided on one end portion side of the switching gear shaft 52. The switching gear 51 configures a gear train Gt illustrated in FIG. 4D by the gear 43*g* of the meshing portion 43 of the above-described bending wheel 41 and the drive gear 33 fixedly provided at the motor shaft 32*a*.

As illustrated in FIG. 4B, an engagement projection 52*a* that protrudes in a direction orthogonal to the switching gear shaft 52 is provided at the other end portion of the shaft 52. The cam ring 53 has a ring cam groove 53*a* formed therein. Further, a ring projection 53*b* protrudes from an outer peripheral surface of the cam ring 53. The switching knob 16 has a cylindrical portion 16*a*, and a cylindrical cam groove 16*b* is formed in the cylindrical portion 16*a*.

On an inner peripheral surface side of the cylindrical portion 16*a* of the switching knob 16, the outer peripheral surface side of the cam ring 53 is disposed. In the arrangement state, the ring projection 53*b* is arranged in the cylindrical cam groove 16*b*. Meanwhile, the engagement projection 52*a* is disposed on an inner peripheral surface side of the cam ring 53. In the arrangement state, the engagement projection 52a is arranged in the ring cam groove 53a.

According to the above-described configuration, the ring projection 53b in the cylindrical cam groove 16b is moved along with rotation of the switching knob 16, and the cam ring 53 is moved in an axial direction of the switching gear shaft 52. In addition, the engagement projection 52a in the ring cam groove 53a is moved in the axial direction along with the movement of the cam ring 53 in the axial direction.

Figure 4D:
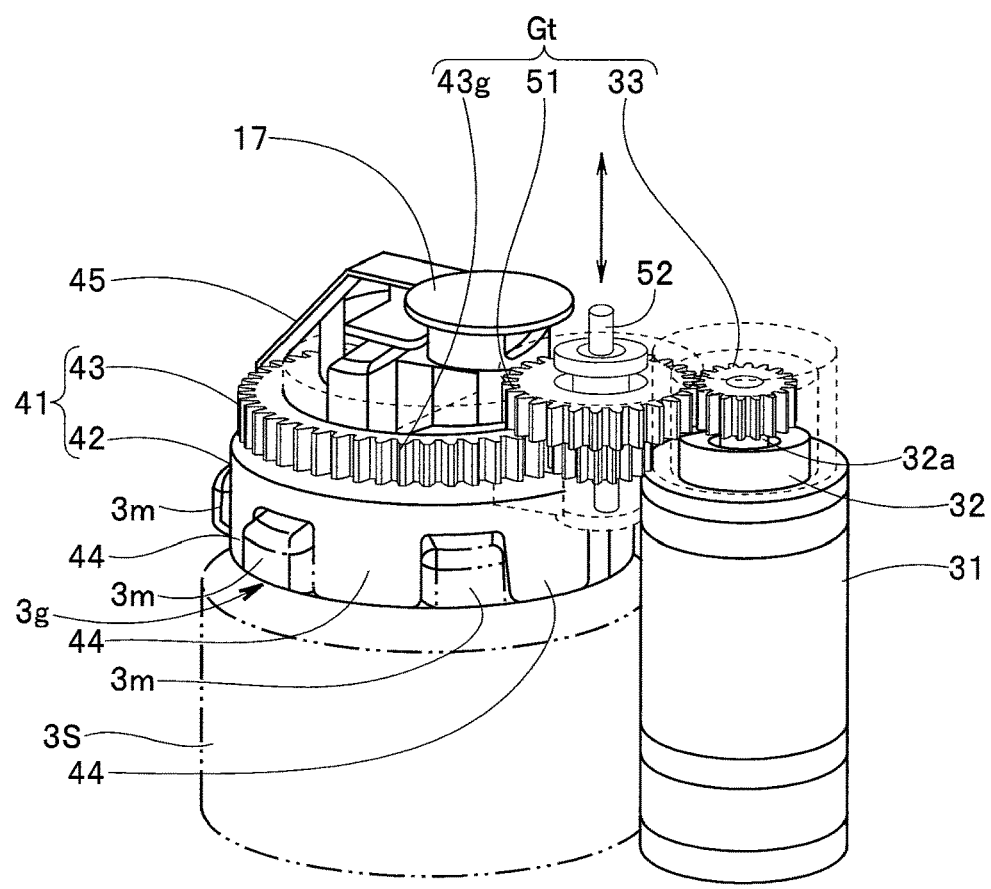
FIG. 4D is a diagram illustrating a gear train configured by a switching gear and a gear of a meshing portion and a drive gear fixedly provided at a motor shaft.

As a result, as illustrated in FIG. 4D, the switching gear 51 of the gear train Gt is moved relative to the axial direction of the switching gear shaft 52 in accordance with the switching operation of the switching knob 16 in the clockwise direction or the counterclockwise direction. As a result, the gear is switched between a state in which the switching gear 51 meshes with the gear 43g of the meshing portion 43 and the drive gear 33 and a state in which they are disconnected from each other.

Then, in the transmission state in which the switching gear 51 meshes with the gear 43g of the meshing portion 43 and the drive gear 33, a rotational driving force of the motor 32 is transmitted to the bending wheel 41, and then the second UD knob 3g is rotated. In other words, the driving force of the motor 32 is not transmitted to the bending wheel 41 by causing the switching gear 51 and the gear 43g of the meshing portion 43 and the drive gear 33 to be in the disconnected state.

Figure 4E:
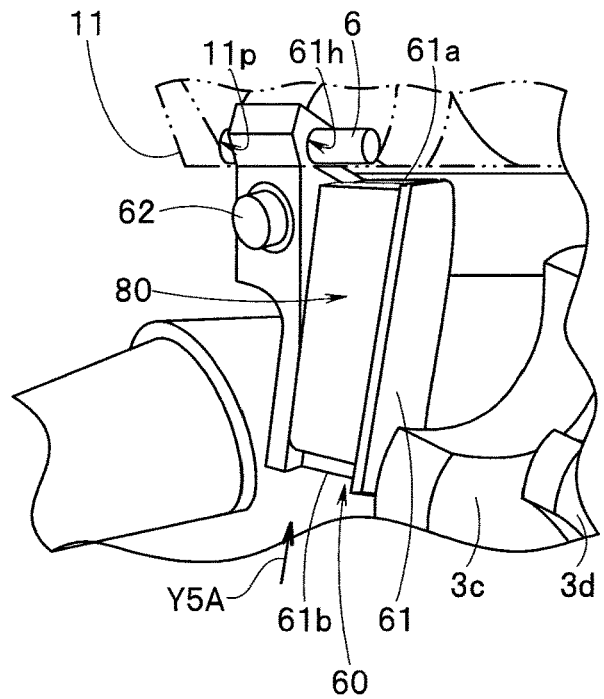
FIG. 4E is a diagram illustrating an operation switch attached so as to rotate to a housing case.

As illustrated in FIG. 4E, the switch main body 61 included in the operation switch 60 is rotatably arranged with respect to the housing case 11 by a hinge pin 6. Specifically, a hinge hole 11p is provided in the housing case 11, and a hinge pin hole 61h is provided in the switch main body 61. The hinge pin 6 passes through the hinge hole 11p and is arranged in the hinge pin hole 61h, whereby the switch main body 61 is pivotally supported in a rotatable manner by the housing case 11 on one end side of the switch main body 61.

The operation switch 60 in which the cover 80 covering the operating element is provided in the switch main body 61 will be described with reference to FIG. 5A to FIG. 7B.

Figure 5A:
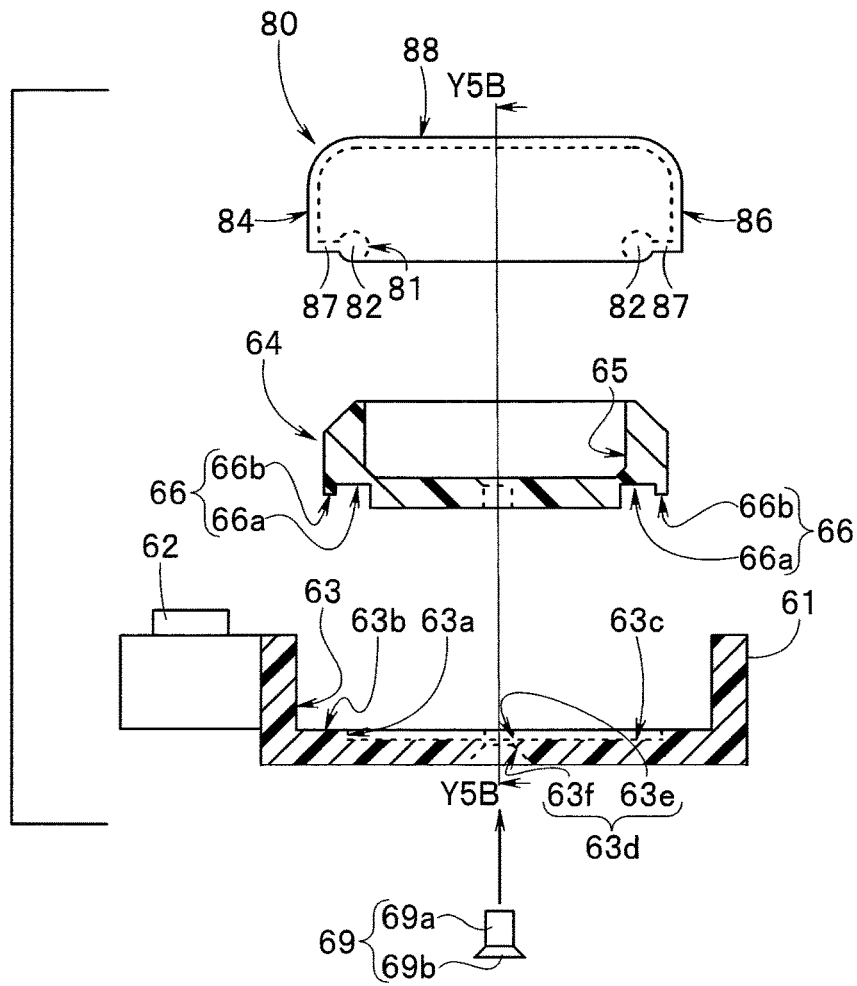
FIG. 5A is a diagram illustrating a switch main body, a switch case, and a cover included in the operation switch.
Figure 5B:
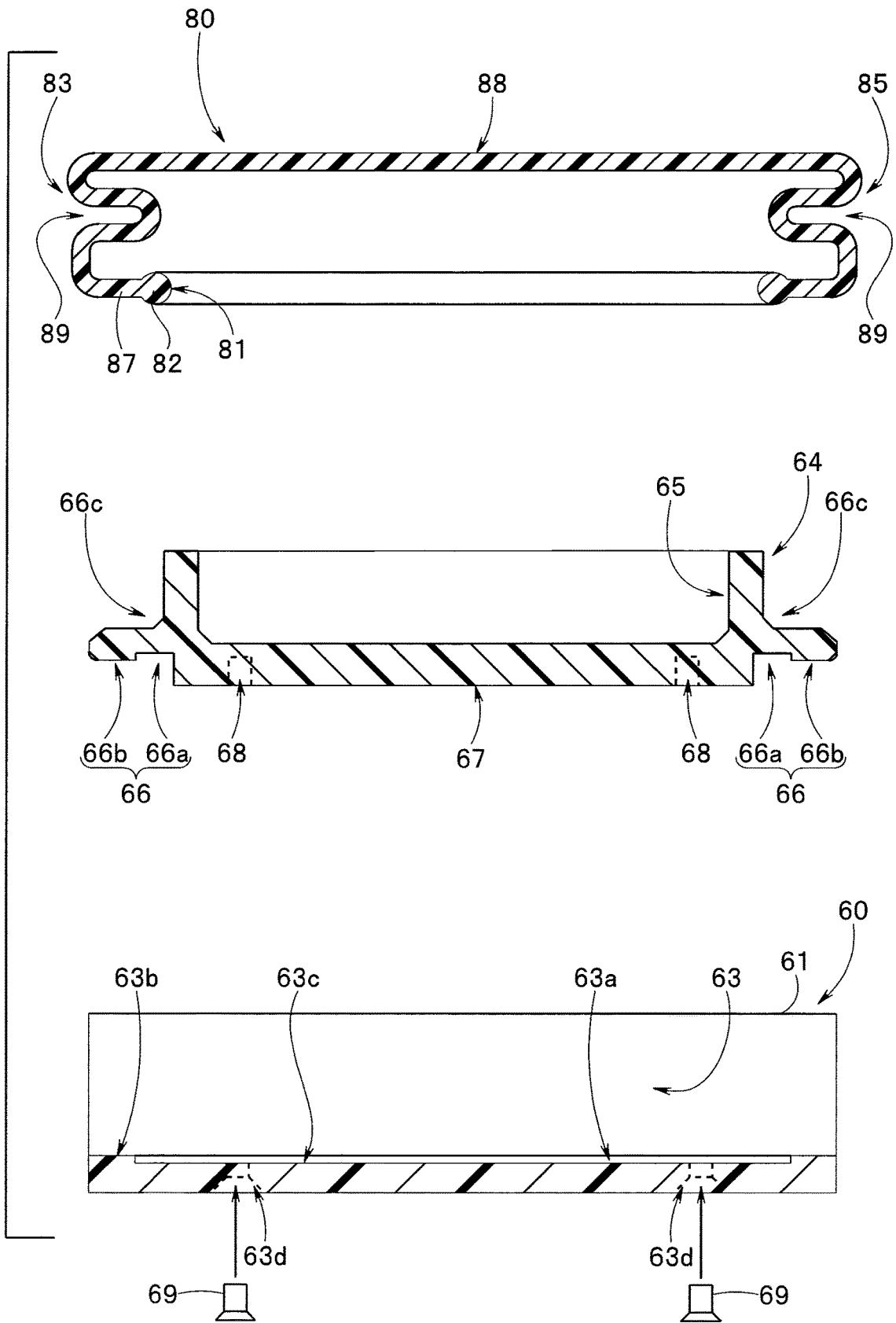
FIG. 5B is a diagram illustrating the switch main body, the switch case, and the cover as viewed from a direction of an arrow 5B in FIG. 5A.

As illustrated in FIGS. 5A and 5B, the operation switch 60 includes the switch main body 61, a switch case 64 in which the operating element is disposed, and the cover 80 provided in the switch case 64.

First, the switch main body 61 will be described.

The switch main body 61 is made of resin. The switch main body 61 is provided with a switch case housing portion 63. The switch case housing portion 63 is a groove elongated in a longitudinal direction. Reference numeral 63a denotes a recess, and the cross-sectional shape thereof is a rectangular shape. The recess 63a is set to have a predetermined depth dimension from a housing portion bottom surface 63b of the switch case housing portion 63. Reference numeral 63c denotes a recess bottom surface. An installation surface 67, which will be described later, is installed on the recess bottom surface 63c.

Reference numeral 63d denotes a screw arrangement hole. The screw arrangement hole 63d has a shaft hole 63e and a countersunk portion 63f. An opening on the shaft hole 63e side is provided at a predetermined position on the recess bottom surface 63c, and an opening on the countersunk portion 63f side is provided on an outer surface on a side opposite to the recess bottom surface 63c.

A shaft portion 69a in which a male screw of a fixing screw 69 is formed is inserted through the shaft hole 63e. A screw head 69b of the fixing screw 69 is arranged at the countersunk portion 63f.

Figure 7A:
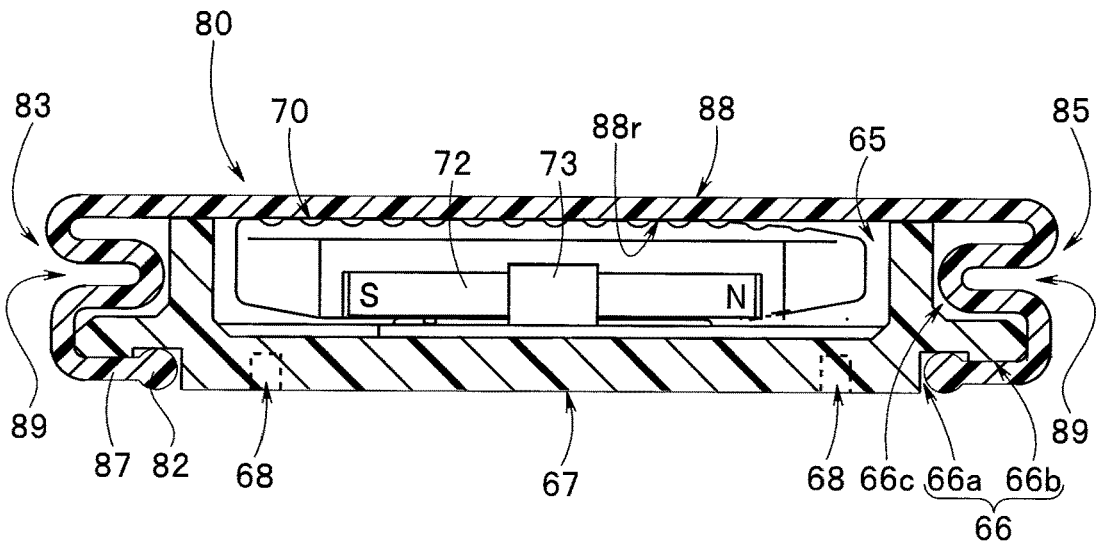
FIG. 7A is a diagram illustrating a state in which the cover is arranged in the switch case in which the operating element is arranged.

As illustrated in FIG. 7A, the switch case 64 in a state in which the cover 80 is disposed is disposed in the switch case housing portion 63.

Next, the cover 80 will be described.

The cover 80 illustrated in FIG. 5A and FIG. 5B is made of elastomer, which is flexible and can serve as an anti-slip portion. The cover 80 is formed as a cover surface having no concave-convex portion in consideration of cleaning properties. In the present embodiment, the cover 80 is preferably a fluoro-rubber having excellent chemical resistance to a cleaning agent or an antiseptic agent.

The cover 80 is formed in a substantially rectangular parallelepiped box shape and having an opening 81 on one surface side thereof. The cover 80 is set to have a predetermined thickness in consideration of operability.

An O-ring shaped portion 82 having a circular cross-sectional shape is provided on an end side of the opening 81. The O-ring shaped portion 82 and respective side wall surface portions 83, 84, 85, and 86 are connected to each other by a cover close contact surface portion 87. The cover close contact surface portion 87 is a fold portion folded at approximately 90 degrees in an inward direction with respect to the respective side wall surface portions 83, 84, 85, and 86.

Reference numeral 88 denotes a finger contact surface, on which the user's finger is placed. The side wall surface portions 83 and 85 are end portions in the longitudinal direction of the cover 80. Bellows-shaped portion 89 is formed in the side wall surface portions 83 and 85 provided on sides in the longitudinal direction. The bellows-shaped portion 89 is a flexure portion provided so as to have a predetermined function in a predetermined shape, which is easily bent and has a predetermined restoring force.

Next, the switch case 64 will be described.

The switch case 64 is a case body made of a resin. The switch case 64 is provided with a recess for disposing an operating element (hereinafter referred to as an operating element recess) 65. The operating element 70 is slidably disposed in the operating element recess 65 so as to slide in the longitudinal direction.

The switch case 64 is provided with a pressing portion 66. The pressing portion 66 includes an O-ring portion housing recess 66a and a cover pressing surface 66b. The O-ring shaped portion 82 of the cover 80 is arranged in the O-ring portion housing recess 66a. In a state in which the O-ring shaped portion 82 is arranged in the O-ring portion housing recess 66a, an opening side of the switch case 64 is covered by a portion of the cover 80 that configures the finger contact surface 88.

Note that, when the O-ring shaped portion 82 of the cover 80 is arranged in the O-ring portion housing recess 66a, the cover close contact surface portion 87 of the cover 80 is arranged on the cover pressing surface 66b. In the arrangement state, the bellows-shaped portion 89 of the cover 80 is disposed in a bellows housing step portion denoted by reference numeral 66c. The bellows housing step portion 66c is formed so as to be located on operating element ends 71a and 71b side, which will be described later.

As described above, the cover close contact surface portion 87 of the cover 80 disposed in the switch case 64 is arranged on the housing portion bottom surface 63b, and the O-ring shaped portion 82 is arranged on the recess bottom surface 63c.

Reference numeral 67 denotes the installation surface, and the installation surface 67 is to be arranged on the recess bottom surface 63c. The installation surface 67 is provided with a plurality of, for example, two female screw portions 68 corresponding to the screw arrangement holes 63d. The shaft portion 69a of the fixing screw 69 is screwed to the female screw portion 68.

Figure 6:
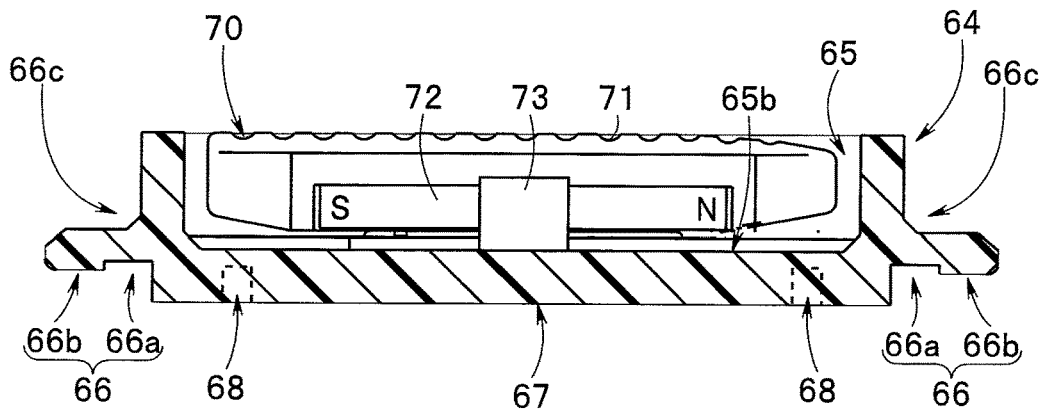
FIG. 6 is a diagram illustrating the switch case and an operating element arranged in an operating element recess of the switch case.

As illustrated in FIG. 6, an operating element 70 is disposed in the operating element recess 65 of the switch case 64 described above. The operating element 70 is a slider, and functions as a so-called slide switch.

An operation surface 71 of the operating element 70 is provided with a concave-convex portion that serves as an anti-slip portion. The operation surface 71 protrudes outward from an opening of the operating element recess 65 by a predetermined amount. A magnet 72 is disposed at a predetermined position of the operating element 70. A hole sensor (hereinafter, shortly referred to as a sensor) 73 is provided at a predetermined position on a bottom surface 65b of the operating element recess 65 of the switch case 64.

The sensor 73 detects a magnetic field of the magnet 72. The sensor 73 outputs a predetermined drive control signal to the motor according to a change in distance between the N pole and the S pole of the magnet 72.

Here, the assembling of the operation switch 60 will be described.

As illustrated in FIG. 6, the cover 80 is attached to the switch case 64 in which the operating element 70 is disposed. As described above, the cover 80 is attached by arranging the O-ring shaped portion 82 in the O-ring portion housing recess 66a, arranging the cover close contact surface portion 87 on the cover pressing surface 66b, and arranging the bellows-shaped portion 89 in the bellows housing step portion 66c.

As a result, as illustrated in FIG. 7A, a state in which a back surface 88r of the finger contact surface 88 of the cover 80 is arranged on the operation surface 71 of the operating element 70 is prepared.

Next, the switch case 64 to which the cover 80 is attached is arranged in the switch case housing portion 63 of the switch main body 61. At the time, the O-ring shaped portion 82 is arranged on the recess bottom surface 63c in the recess 63a.

Figure 7B:
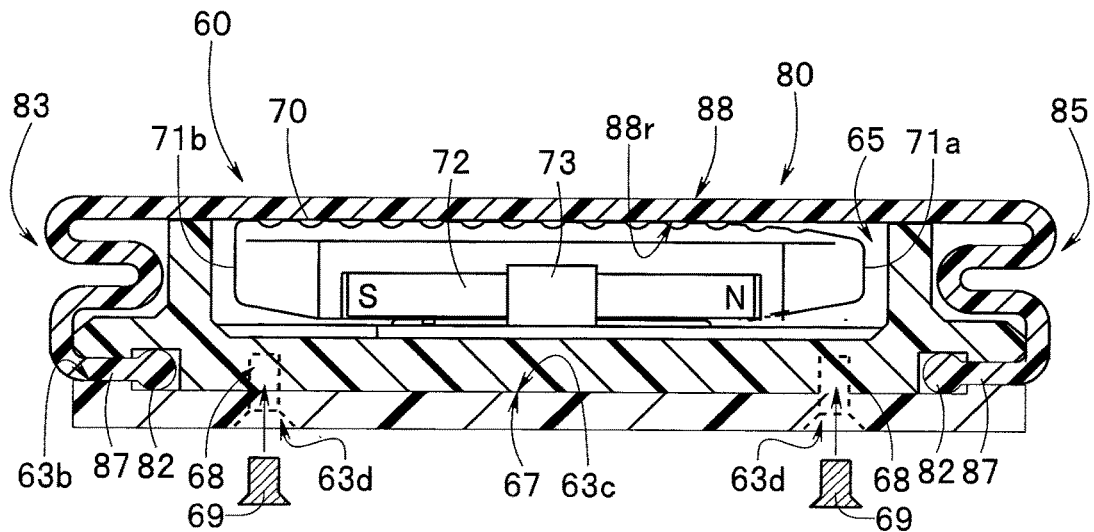
FIG. 7B is a diagram illustrating the operation switch in which the operating element is covered with the cover.

As a result, as illustrated in FIG. 7B, the cover close contact surface portion 87 is arranged so as to be in contact with or to face the housing portion bottom surface 63b. Further, the installation surface 67 is arranged so as to be in contact with or to face the recess bottom surface 63c. At the time, a position of the female screw portion 68 and a position of the screw arrangement hole 63d are made substantially coincident with each other.

After that, the fixing screw 69 is inserted into the screw arrangement hole 63d as indicated by an arrow, and the shaft portion 69a of the fixing screw 69 is screwed to the female screw portion 68. Then, the pressing portion 66 of the switch case 64 is moved toward the housing portion bottom surface 63b side, and the installation surface 67 is moved toward the recess bottom surface 63c side.

As a result, the installation surface 67 is disposed in abutment with the recess bottom surface 63c, and the O-ring shaped portion 82 and the cover close contact surface portion 87 are changed in a predetermined elastic deformation state, so that a watertightness between the switch case 64 and the switch main body 61 is maintained to achieve a state in which the operating element 70 is arranged in a watertight space of the operation switch 60.

In the present embodiment, the operating element 70 is operated by the user through the cover 80.

Specifically, the user places a finger on the finger contact surface 88 of the cover 80, and applies the back surface 88r of the finger contact surface 88 against the operation surface 71 while pressing the finger against the finger contact surface 88 to perform a sliding operation. Then, the finger contact surface 88 and the operation surface 71 are slid in accordance with the user's operation, and the bellows-shaped portion 89 is elastically deformed along with the sliding movement against the elastic force.

For example, supposing that the operating element 70 illustrated in FIG. 7B is moved toward a case main body lower end 61b side in FIG. 4E. It is assumed that the operating element lower end 71b illustrated in FIG. 7B is located at the lowermost part in a sliding range of the operating element recess 65.

Then, the sensor 73 outputs a first drive control signal to the motor 32. As a result, the motor 32 is rotationally driven at a high speed, for example, and rotates the second UD knob 3g in the counterclockwise direction.

During the sliding operation, the bellows-shaped portion 89 of the lower side wall surface portion 83 and the bellows-shaped portion 89 of the upper side wall surface portion 85 are elastically deformed respectively corresponding to the sliding movement.

Note that the sensor 73 outputs a second drive control signal to the motor 32 when the operating element lower end 71b is spaced apart from an intermediate portion by a predetermined distance toward the case main body lower end 61b side. Then, the motor 32 is rotationally driven at a low speed, for example, and rotates the second UD knob 3g in the counterclockwise direction. During the sliding operation, the bellows-shaped portion 89 of the lower side wall surface portion 83 and the bellows-shaped portion 89 of the upper side wall surface portion 85 are elastically deformed respectively corresponding to the sliding movement.

On the contrary, when the operating element end 71a is located at the uppermost part in the sliding range of the operating element recess 65, the sensor 73 outputs a third drive control signal to the motor 32. As a result, the motor 32 is rotationally driven at a high speed, for example, and rotates the second UD knob 3g in the clockwise direction.

Then, when the operating element upper end 71a is spaced apart from the intermediate portion by a predetermined distance toward the case main body upper end 61a side, the sensor 73 outputs a fourth drive control signal to the motor 32. At the time, the motor 32 is rotationally driven at a low speed, for example, and rotates the second UD knob 3g in the clockwise direction.

Also in these operation states, the bellows-shaped portion 89 of the lower side wall surface portion 83 and the bellows-shaped portion 89 of the upper side wall surface portion 85 are elastically deformed respectively corresponding to the sliding movement.

The user separates the finger from the finger contact surface 88, whereby the operating element 70 is returned to the intermediate portion by the restoring force of the bellows-shaped portion 89 of the lower side wall surface portion 83 and the bellows-shaped portion 89 of the upper side wall surface portion 85.

After an endoscopy is finished, the endoscope 1 and the endoscope external mechanism 10 are cleaned. In the endoscope external mechanism 10 of the present embodiment, the operating element 70 included in the operation switch 60 is covered with the cover 80 having no unevenness on the surface thereof.

Therefore, dirt is less likely to accumulate on the finger contact surface 88 of the cover 80. In addition, the surface of the cover 80 is a smooth surface having no unevenness. Therefore, when the surface of the cover 80 including the bellows-shaped portion 89 is cleaned, dirt can be quickly and easily removed.

As a result, cleaning of the operation switch 60 provided in the housing case 11 is easily and reliably performed, whereby enabling to easily clean the endoscope external mechanism 10.

Note that, in the above-described embodiment, the back surface 88r of the finger contact surface 88 of the cover 80 is substantially integrated with the operation surface 71 by the cover 80, which has adhesion and serves as an anti-slip portion, in a state in which the back surface 88r is disposed on the operation surface 71 of the operating element 70. Therefore, depending on a material of the cover 80, there has been a possibility that a slippage occurs between the back surface of the finger contact surface 88 and the operation surface 71, and a problem occurs during the sliding operation.

Figure 8A:
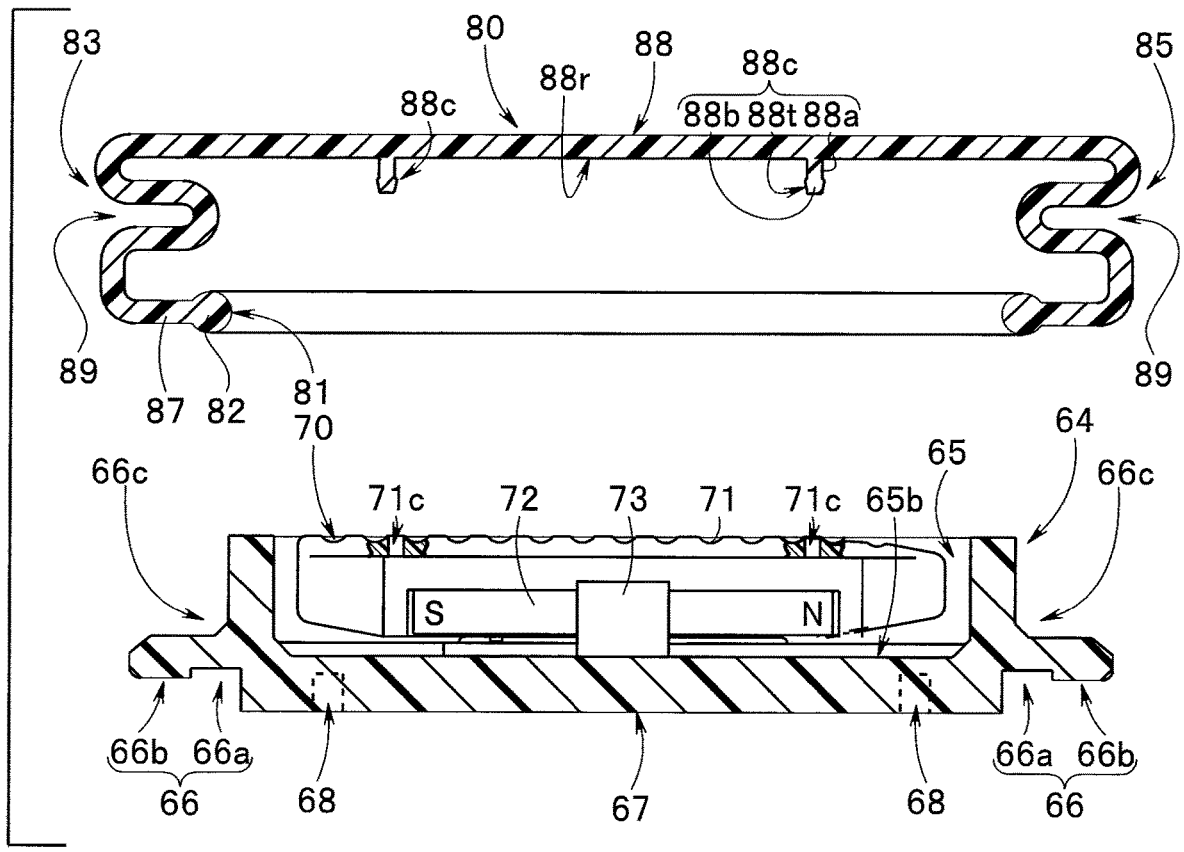
FIG. 8A is a diagram illustrating a projection portion provided on a back surface of a finger contact surface of the cover and a locking hole portion provided on an operation surface side of the operating element.

In order to solve the problem, as illustrated in FIG. 8A, a plurality of projection portions 88c that protrudes from the back surface 88r toward the operation surface 71 side of the operating element 70 are provided on the back surface 88r of the finger contact surface 88, which is a part of the cover 80. Meanwhile, a fitting hole portion 71c that functions as an engaging portion is provided in an operating element upper surface forming portion including the operation surface 71 of the operating element 70. Note that instead of providing the fitting hole portion 71c of the through-hole, a bottomed fitting recess may be provided.

Figure 8B:
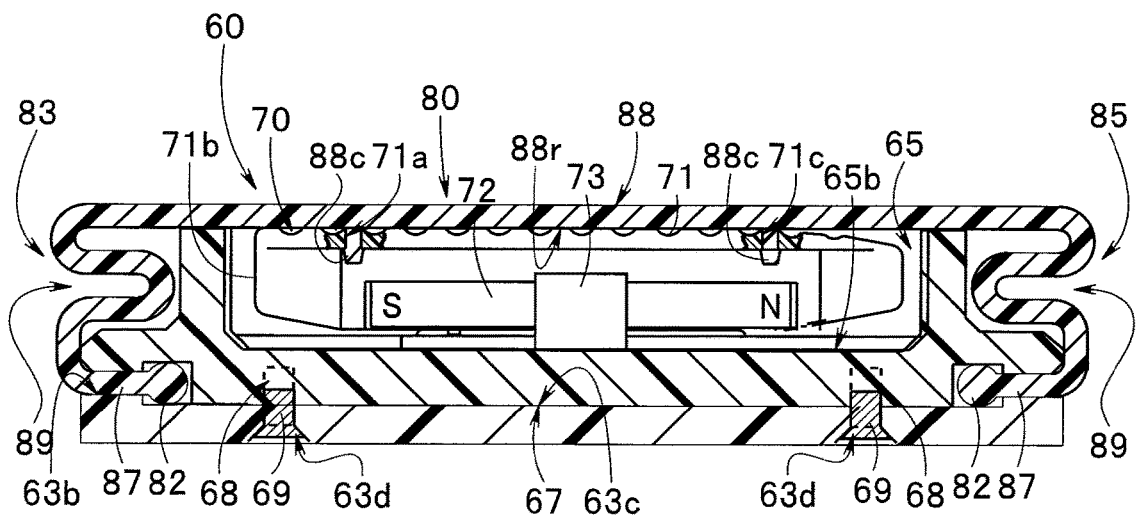
FIG. 8B is a diagram illustrating the operation switch in which the finger contact surface of the cover and the operation surface of the operating element are integrally fixed to each other due to an engagement.

The projection portion 88c has a shaft portion 88a and a fixing portion 88b including a tapered surface 88t having a diameter larger than that of the shaft portion 88a and having a tapered shape. The fixing portion 88b having the tapered surface 88t passes through an inside of the fitting hole portion 71c while being reduced in diameter, and after passing, is restored to its original shape as illustrated in FIG. 8B, and the projection portion 88c is fitted to a back surface of the operation surface 71 to be arranged.

As a result, the finger contact surface 88 of the cover 80 and the operation surface 71 of the operating element 70 are integrally fixed by engagement between the projection portion 88c and the fitting hole portion 71c.

Therefore, the user places a finger on the finger contact surface 88 of the cover 80, and by performing a sliding operation on the finger contact surface 88 with the finger, the finger contact surface 88 and the operation surface 71 of the operating element 70, which are integrated by engaging with the projection portion 88c, are integrally moved, whereby the user can perform an operation for smoothly sliding the operating element 70.

According to the configuration, the occurrence of slippage between the back surface of the finger contact surface 88 and the operation surface 71 due to the difference in the material of the cover 80 is reliably eliminated, so that an improved sliding operability can be achieved. Further, an amount of operating power when performing a sliding operation on the operating element 70 through the cover 80 is reduced, and thus it is possible to obtain smoother operability.

Note that a protruding portion that protrudes toward the cover 80 side may be provided on the operation surface 71 side of the operating element 70, and a bottomed fitting recess may be provided on the back surface 88r of the cover 80 to obtain the same function and effect.

Figure 9A:
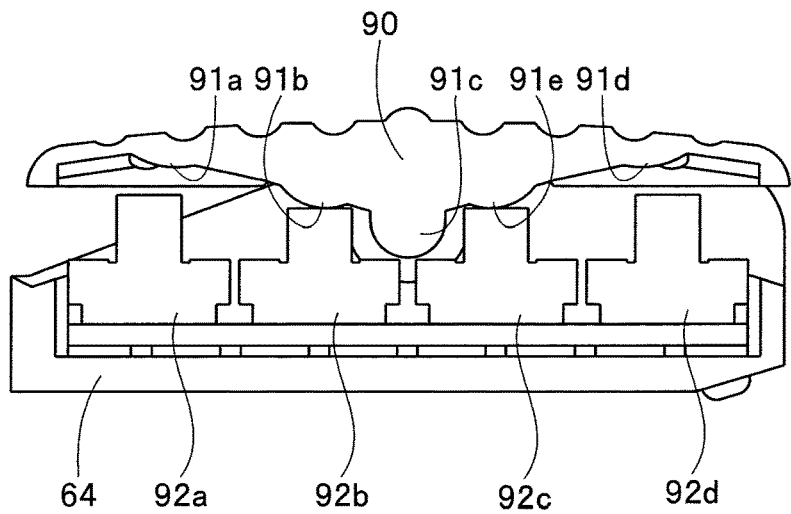
FIG. 9A is a diagram illustrating an example of a configuration in which the operating element is a seesaw switch.

Further, in the above-described embodiment, the operating element 70 disposed in the operating element recess 65 of the switch case 64 is as a slide switch. However, the operating element 70 may be a seesaw switch 90 that rotates clockwise or counterclockwise with a central convex portion 91c as a fulcrum, as illustrated in FIG. 9A.

In the seesaw switch 90, four switch convex portions 91a, 91b, 91d, and 91e are provided. In addition, a plurality of, for example, four tactile switches 92a, 92b, 92c, and 92d are provided in the operating element recess 65.

When the seesaw switch 90 is in an initial state, a second tactile switch 92b and a third tactile switch 92c are in an ON state, and a first tactile switch 92a and a fourth tactile switch 92d are in an OFF state. At the time, the motor 32 is in a stopped state.

Figure 9B:
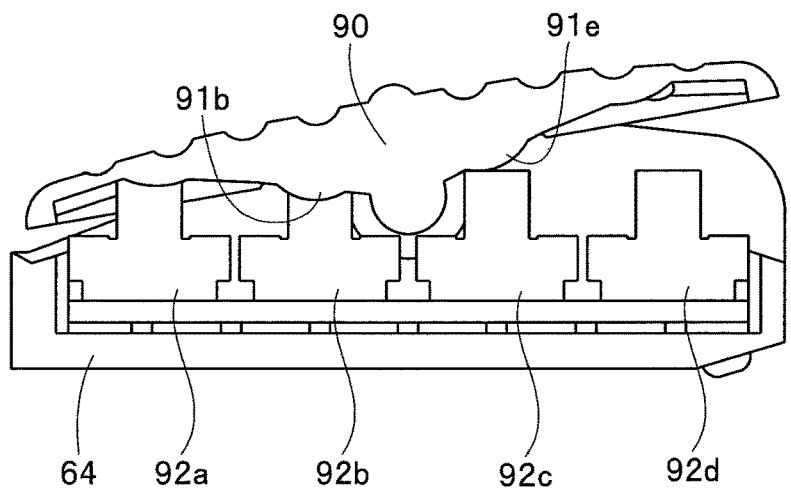
FIG. 9B is a diagram illustrating an example of an operation of the seesaw switch.

When the seesaw switch 90 is rotated counterclockwise, as illustrated in FIG. 9B, the third tactile switch 92c is switched from ON to OFF, and when only the second tactile switch 92b is in the ON state, the second drive control signal is output to the motor 32. Then, the motor 32 is driven at a low speed so as to rotate the second UD knob 3g in the counterclockwise direction.

Figure 9C:
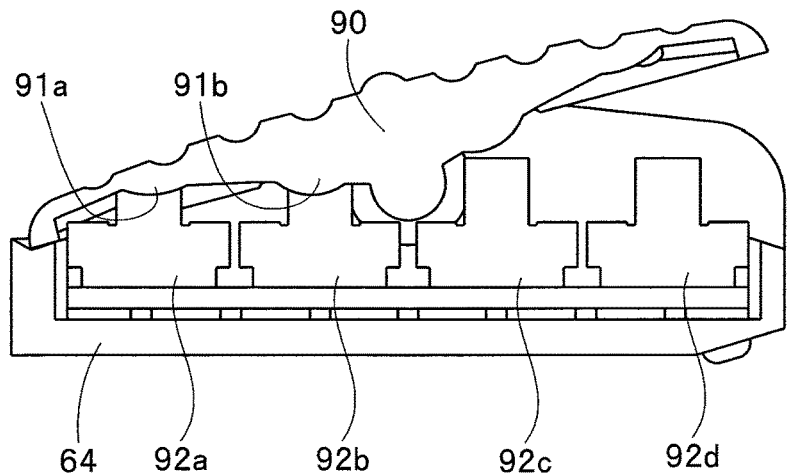
FIG. 9C is a diagram illustrating another example of the operation of the seesaw switch.

Then, as illustrated in FIG. 9C, the seesaw switch 90 is further rotated counterclockwise, so that the first tactile switch 92a is turned on in addition to the second tactile switch 92b. Then, the first drive control signal is output to the motor 32. Then, the motor 32 is driven at a high speed so as to rotate the second UD knob 3g in the counterclockwise direction.

Note that, although not illustrated, the second tactile switch 92b is switched from ON to OFF when the seesaw switch 90 is rotated clockwise while the motor 32 is in the stopped state, and only the third tactile switch 92c is turned on, and the fourth drive control signal is output to the motor 32. Then, the motor 32 is driven at a low speed so as to rotate the second UD knob 3g in the clockwise direction.

After that, the seesaw switch 90 is further rotated clockwise, so that the fourth tactile switch 92d is turned on in addition to the third tactile switch 92c. Then, the third drive control signal is output to the motor 32. Then, the motor 32 is driven at a high speed so as to rotate the second UD knob 3g in the clockwise direction.

Although not illustrated, in the above-described seesaw switch 90, the cover 80 is provided in the switch case 64, and the seesaw switch 90 is covered.

As described above, the drive control signal is output to the motor 32 by performing a slide operation or a rotation operation on the operating element 70 provided in the operation switch 60, and the second UD knob 3g is rotationally controlled by the driving force of the motor 32. As a result, the user can cause the second bending portion 2b2 to bend without applying a large load on the finger.

Note that in the above-described embodiment, the speed is set to two stages, i.e., a high speed and a low speed. However, the driving of the motor 32 may be controlled so as to change the speed in one or three or more stages or stepwise on the basis of a detection result of the hole sensor 71. Further, the number of tactile switches and the number of the switch convex portions may be increased or decreased, and thus the speed may be changed in one stage or three or more stages.

Note that in the above-described embodiment, the speed is set to two stages, i.e., a high speed and a low speed. However, the driving of the motor 32 may be controlled so as to change the speed in one or three or more stages or stepwise on the basis of a detection result of the hole sensor 73. Further, the number of tactile switches and the number of the switch convex portions may be increased or decreased, and thus the speed may be changed in one stage or three or more stages.

The attachment of the endoscope external mechanism 10 to the sub-operation portion 3S will be described with reference to FIG. 10A to FIG. FIG. 10D.

In attaching the housing case 11 of the endoscope external mechanism 10 to the sub-operation portion 3S, the user checks whether or not the second UD fixing knob 3*h* provided in the second UD knob 3*g* in advance is in the free position.

Figure 10A:
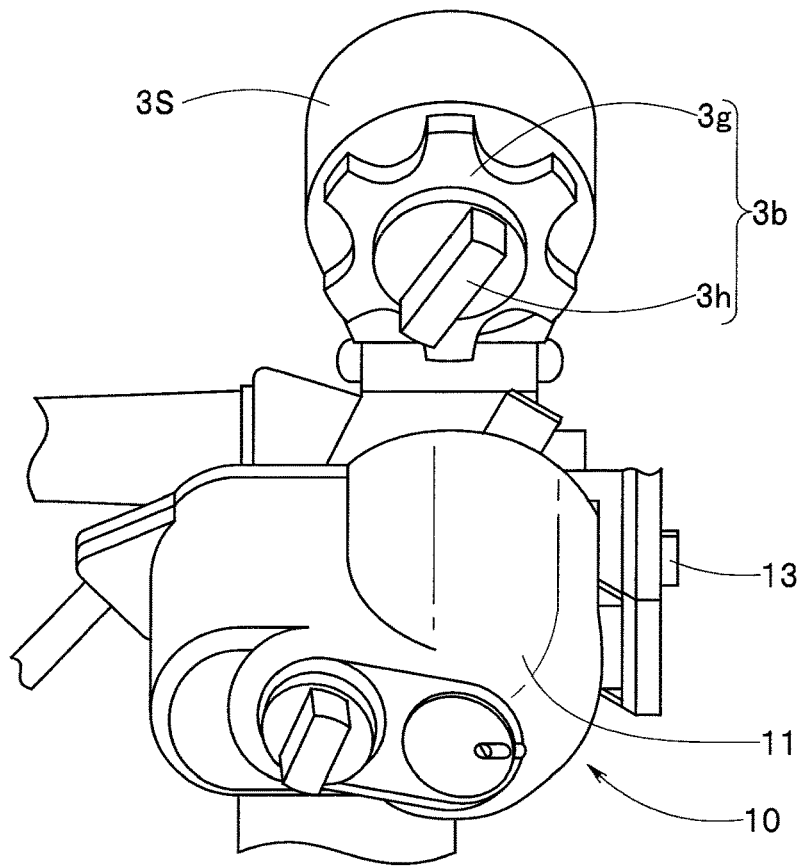
FIG. 10A is a diagram illustrating a state in which the housing case of the endoscope external mechanism is attached to the sub-operation portion.

After checking that the second UD fixing knob 3*h* is arranged in the free position, the user causes the housing case 11 of the endoscope external mechanism 10 to face the second UD knob 3*g* provided in the sub-operation portion 3S, as illustrated in FIG. 10A. At the time, the user causes the bending wheel 41 of the knob rotating portion 40, which is disposed in the case inner space, to face the second UD knob 3*g*.

Next, the user brings the housing case 11 closer to the second UD knob 3*g*. Then, the user causes the lever recess 25 provided in the rotation mechanism portion main body 21 to face the second UD fixing knob 3*h*, and houses the second UD fixing knob 3*h* in the lever recess 25 as illustrated in FIG. 4C. As a result, as illustrated in FIG. 2B, the housing case 11 is arranged on the second UD knob 3*g*.

In the housing arrangement state, as illustrated in FIG. 4C, the convex portion 44 of the knob connecting portion 42 is disposed in the recess of the second UD knob 3*g* in a predetermined state, and the second UD knob 3*g* and the bending wheel 41 are integrated with each other.

Here, the user engages and fixes the locking claw portion 15 of the hinge portion 14 to the locking portion 13, as illustrated in FIG. 2C and FIG. 2D. As a result, as illustrated in FIG. 10B, attachment of the housing case 11 to the sub-operation portion 3S is completed.

Figure 10B:
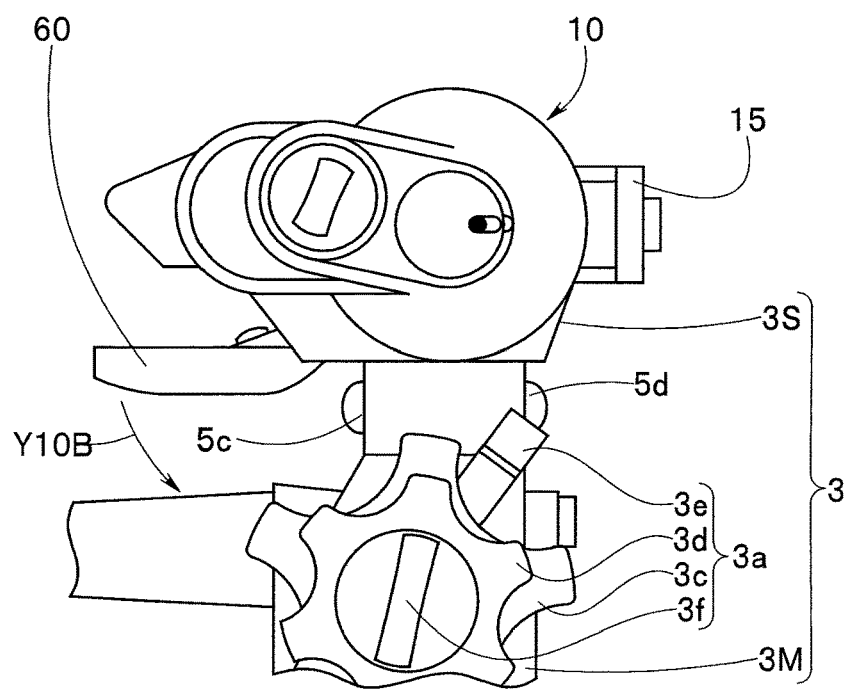
FIG. 10B is a diagram illustrating a done state in which the housing case is completely attached to the sub-operation portion and an initial position of the operation switch in the done state.

As illustrated in FIG. 10B, the remote switch 5*c* is exposed due to the operation switch 60 being arranged at the initial position, in a state in which the housing case 11 is attached to the sub-operation portion 3S.

After attaching the housing case 11 to the sub-operation portion 3S, the user pushes down the switch main body 61 of the operation switch 60, which is rotatable to the housing case 11, in a direction of an arrow Y10B, as illustrated in FIG. 10B.

Figure 10C:
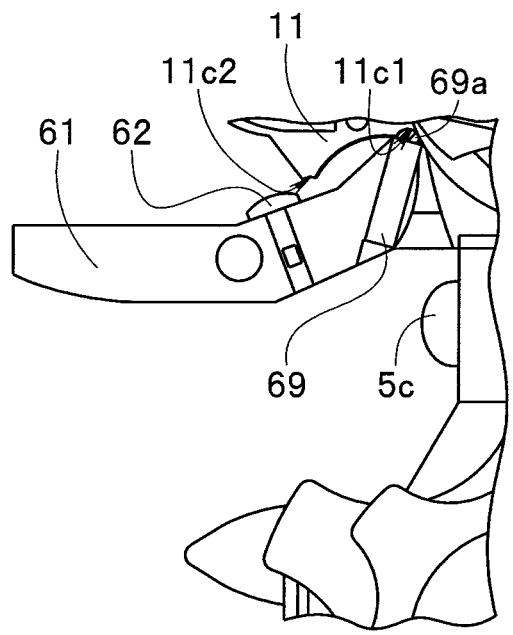
FIG. 10C is a diagram illustrating a first engagement state in which a sliding convex portion of a ball spring plunger is arranged in a first recess of the housing case.
Figure 10D:
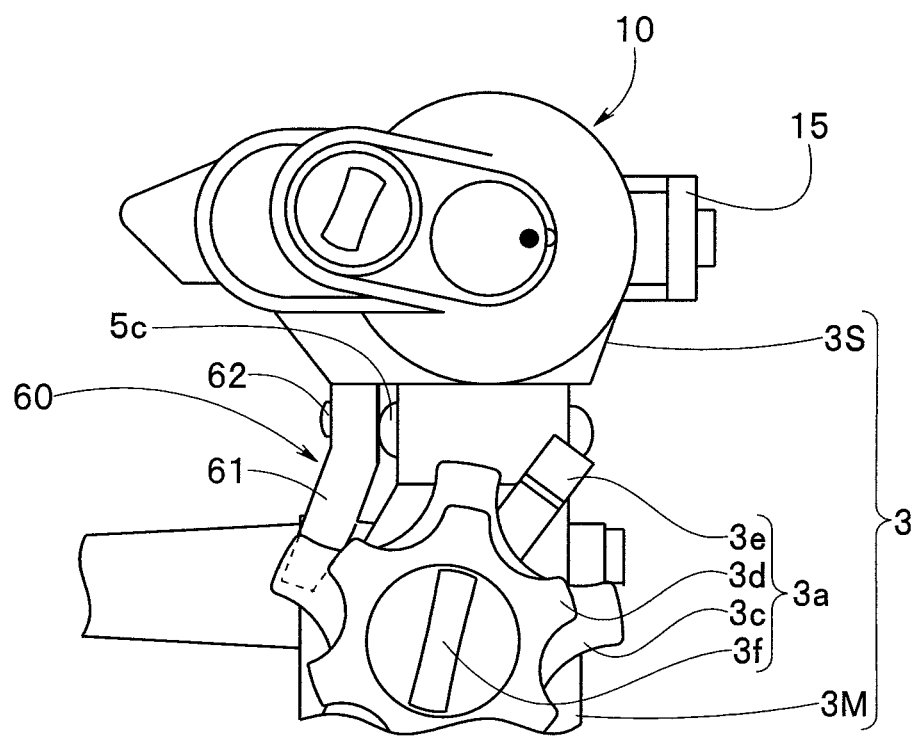
FIG. 10D is a diagram illustrating a mechanism mounted state in which the operation switch of the endoscope external mechanism is disposed adjacent to a first bending operation device provided in a main operation portion.

Then, as illustrated in FIG. 10C, a first engagement state of the sliding convex portion 69*a* of the ball spring plunger 69 provided in the switch main body 61 and a first recess 11*c*1 of the housing case 11 is released, and then the switch main body 61 moves toward a portion between one surface of the main operation portion 3M and one end surface of the first UD knob 3*c* illustrated in FIG. 10D.

After that, the sliding convex portion 69*a* of the ball spring plunger 69 and a second recess 11*c*2 of the housing case 11 illustrated in FIG. 10C are engaged with each other and brought into a second engagement state, and thus the movement of the operation switch 60 is completed as illustrated in FIG. 10D. In other words, the operation switch 60 of the endoscope external mechanism 10 is disposed in a first position adjacently provided to the first bending operation device 3*a* provided in the main operation portion 3M.

As a result, the exposed remote switch 5*c* is covered by the switch main body 61. At the time, a remote switch side of a dummy switch 62 is arranged on the remote switch 5*c*. In the state, the remote switch 5*c* can be operated by pressing the dummy switch 62 so as to move along in a thickness direction of the switch main body 61.

Here, a function of the endoscope 1 in which the endoscope external mechanism 10 is attached to the sub-operation portion 3S and the operation switch 60 is disposed adjacent to the first bending operation device 3*a* will be described.

When the user performs endoscopy with the endoscope 1 in which the endoscope external mechanism 10 is attached to the sub-operation portion 3S, the user grasps the main operation portion 3M. Then, the user grasps the insertion portion 2 with a hand different from the hand holding the main operation portion 3M, and inserts the insertion portion 2 into the body through, for example, the oral cavity.

At the time, the user appropriately causes the first bending portion 2*b*1 and the second bending portion 2*b*2 to bend. In other words, the user appropriately rotationally operates the first UD knob 3*c* or the first RL knob 3*d* of the first bending operation device 3*a* provided in the main operation portion 3M and causes the first bending portion 2*b*1 to bend in the up-down direction or the right-left direction, while appropriately operating the operating element 70 of the operation switch 60 adjacently provided to the first bending operation device 3*a* of the main operation portion 3M through the cover 80 and causing the second bending portion 2*b*2 to bend in the up-down direction.

As described above, the operation switch 60 is adjacently provided to the first bending operation device 3*a* of the main operation portion 3M. As a result, the user can smoothly perform the rotation operation of the first UD knob 3*c* and the first RL knob 3*d* of the first bending operation device 3*a*, the operation of sliding the operating element 70 over the cover 80 of the operation switch 60, and the like by the finger of the hand of the user who grasps the main operation portion 3M.

Further, the user can more smoothly perform the insertion of the insertion portion 2 into the deeper of the body by slightly moving the finger of the hand without touching the remote switch and appropriately causing the first bending portion 2*b*1 and the second bending portion 2*b*2 provided in the bending portion 2*b* to bend.

Note that, in the above description, the endoscope external mechanism 10 is mounted on the sub-operation portion 3S, and the second bending portion 2*b*2 is bent without applying a large load on the finger of the user. However, the knob on which the endoscope external mechanism 10 is mounted is not limited to the second UD knob 3*g* provided in the sub-operation portion 3S, but may be the first RL knob 3*d* provided in the main operation portion 3M, or both of the first UD knob 3*c* and the first RL knob 3*d*.

The present invention is not limited to the embodiment described above, and various changes and modifications can be made without departing from the spirit and scope of the present invention.

What is claimed is:
1. An external mechanism, comprising:
an engagement member configured to matingly engage with a bending operation knob of a bending operation device provided in an operation portion of an endoscope;
a driving motor configured to generate a driving force for rotating the engagement member;
a housing case housing the engagement member and the driving motor, the housing case being configured to be detachably attached to the operation portion;
an operation switch rotatably connected to the housing case and configured to output a control signal to the driving motor, and a rotation shaft, wherein the operation switch is pivotally supported by the rotation shaft such that the operation switch rotates with respect to the housing case.

2. The external mechanism according to claim 1, wherein the rotation shaft is inserted through a first hole provided in the housing case and a second hole provided in the operation switch.

3. An external mechanism comprising:
an engagement member configured to matingly engage with a bending operation knob of a bending operation device provided in an operation portion of an endoscope;
a driving motor configured to generate a driving force for rotating the engagement member;
a housing case housing the engagement member and the driving motor, the housing case being configured to be detachably attached to the operation portion; and
an operation switch connected to the housing case and configured to output a control signal to the driving motor, wherein
the operation switch includes a dummy switch, and
the dummy switch being disposed to communicate with a remote switch provided in the operation portion of the endoscope such that activation of the dummy switch activates the remote switch.

4. The external mechanism according to claim 3, wherein the dummy switch is arranged on the remote switch due to the operation switch rotating with respect to the housing case.

5. An endoscope apparatus comprising:
an endoscope comprising:
an insertion portion having a bending portion; and
an operation knob configured to operate the bending portion; and
an external mechanism comprising:
an engagement member configured to matingly engage with the operation knob;
a driving motor configured to generate a driving force for rotating the engagement member;
a housing case housing the engagement member and the driving motor, the housing case being configured to be detachably attached to the operation knob;
an operation switch rotatably connected to the housing case and configured to output a control signal to the driving motor, and
a rotation shaft, wherein the operation switch is pivotally supported by the rotation shaft such that the operation switch rotates with respect to the housing case.

6. An endoscope apparatus comprising:
the external mechanism for the endoscope according to claim 3; and
the endoscope comprising:
an insertion portion having a bending portion; and
the operation knob configured to operate the bending portion
wherein the external mechanism is mounted to matingly engage with the bending operation knob.

7. The external mechanism according to claim 1, further comprising:
a dummy switch disposed on the operation switch;
wherein a direction that the dummy switch extends from a surface of the operation switch is substantially perpendicular to a direction that the rotation shaft extends.

8. The external mechanism according to claim 1, wherein the operation switch rotates about the rotation shaft between a first position in which the operation switch is adjacent to the operation portion of the endoscope and a second position in which the operation switch is moved away from the operation portion of the endoscope.

9. The endoscope system according to claim 5, wherein the operation knob rotates relative to a first rotation axis; and
the operation switch rotates relative to the housing case with respect to a second rotation axis, the second rotation axis being parallel to the first rotation axis.

10. The external mechanism according to claim 1, wherein the engagement member having a plurality of first projections for matingly engaging between a corresponding plurality of second projections on the operation knob.

11. The external mechanism according to claim 3, wherein the engagement member having a plurality of first projections for matingly engaging between a corresponding plurality of second projections on the operation knob.

12. The external mechanism according to claim 5, wherein the engagement member having a plurality of first projections for matingly engaging between a corresponding plurality of second projections on the operation knob.

* * * * *